United States Patent
Miller et al.

(10) Patent No.: US 11,717,299 B2
(45) Date of Patent: Aug. 8, 2023

(54) SURGICAL STAPLING DEVICE WITH PROBIOTICS

(71) Applicant: Covidien LP, Mansfield, MA (US)

(72) Inventors: Jeffrey A. Miller, East Haven, CT (US); Haley E. Strassner, Hamden, CT (US); Justin P. Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 98 days.

(21) Appl. No.: 17/499,165

(22) Filed: Oct. 12, 2021

(65) Prior Publication Data
US 2023/0109979 A1    Apr. 13, 2023

(51) Int. Cl.
*A61B 17/064* (2006.01)
*A61B 17/115* (2006.01)
*A61B 17/00* (2006.01)

(52) U.S. Cl.
CPC ... *A61B 17/1155* (2013.01); *A61B 2017/0046* (2013.01); *A61B 2017/00831* (2013.01)

(58) Field of Classification Search
CPC .................. A61B 17/1155; A61B 2017/07257
See application file for complete search history.

(56) References Cited

U.S. PATENT DOCUMENTS

| | | |
|---|---|---|
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshln et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

International Search Report and Written Opinion dated Feb. 13, 2023, issued in corresponding international appln. No. PCT/IB2022/059498, 20 pages.

*Primary Examiner* — Eyamindae C Jallow

(74) *Attorney, Agent, or Firm* — Carter, DeLuca & Farrell LLP

(57) ABSTRACT

A circular stapling device for performing anastomosis procedures includes an end effector that includes or is adapted to deliver probiotics to an anastomotic site during formation of the anastomosis.

20 Claims, 22 Drawing Sheets

(56) References Cited

U.S. PATENT DOCUMENTS

| | | |
|---|---|---|
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |

(56) References Cited

U.S. PATENT DOCUMENTS

| | | |
|---|---|---|
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |

(56) References Cited

U.S. PATENT DOCUMENTS

| | | |
|---|---|---|
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |

(56) References Cited

U.S. PATENT DOCUMENTS

| | | |
|---|---|---|
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0024476 A1 | 2/2011 | Bettuchi et al. |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0241491 A1* | 9/2012 | Aldridge ............ A61B 17/1155 227/175.1 |
| 2012/0241497 A1* | 9/2012 | Mandakolathur Vasudevan ......... A61B 17/07292 227/176.1 |
| 2012/0241499 A1* | 9/2012 | Baxter, III ........ A61B 17/07292 227/176.1 |
| 2012/0241503 A1* | 9/2012 | Baxter, III ........... A61B 17/068 227/176.1 |
| 2012/0248169 A1* | 10/2012 | Widenhouse ....... A61B 17/0644 227/175.1 |
| 2012/0253298 A1* | 10/2012 | Henderson ....... A61B 17/07292 604/93.01 |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0083772 A1 | 3/2015 | Miller et al. |
| 2015/0173763 A1 | 6/2015 | Liu |
| 2015/0209045 A1 | 7/2015 | Hodgkinson et al. |
| 2015/0282809 A1 | 10/2015 | Shelton, IV et al. |
| 2015/0282810 A1* | 10/2015 | Shelton, IV ..... A61B 17/07207 227/180.1 |

(56) References Cited

U.S. PATENT DOCUMENTS

| | | | |
|---|---|---|---|
| 2017/0055986 A1* | 3/2017 | Harris | A61B 17/07207 |
| 2017/0128068 A1 | 5/2017 | Zhang et al. | |
| 2018/0085125 A1 | 3/2018 | Nativ et al. | |

FOREIGN PATENT DOCUMENTS

| CN | 104039244 A | 9/2014 |
|---|---|---|
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1671597 A1 | 6/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2974676 A1 | 1/2016 |
| EP | 3023077 A1 | 5/2016 |
| EP | 3412225 A1 | 12/2018 |
| EP | 3549545 A2 | 10/2019 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9835614 A1 | 8/1998 |
| WO | 0154594 A1 | 8/2001 |
| WO | 02080781 A2 | 10/2002 |
| WO | 2004047654 A2 | 6/2004 |
| WO | 2008107918 A1 | 9/2008 |
| WO | 2019130087 A1 | 7/2019 |

\* cited by examiner

SURGICAL STAPLING DEVICE WITH PROBIOTICS

FIELD

This disclosure generally relates to stapling devices and, more particularly, to circular stapling devices that include probiotics to be delivered to an anastomotic site during formation of an anastomosis.

BACKGROUND

Circular stapling devices for performing surgical procedures such as anastomosis are well known. In an anastomosis procedure, two ends of organ sections are joined with the circular stapling device. Typically, circular stapling devices include a handle assembly, an elongated shaft or adapter assembly, a shell assembly including a staple cartridge, and an anvil assembly that is mountable to the adapter assembly to move in relation to the staple cartridge between open and clamped positions. In use, opposed tissue end sections of the organ sections are clamped between an anvil head of the anvil assembly and the staple cartridge of the cartridge assembly and the device is fired to drive an annular array of staples from the staple cartridge through the tissue end sections for deformation against the anvil head. An annular knife positioned within the shell assembly is simultaneously or subsequently advanced to core or remove organ tissue interior of the staples to clear an internal tubular passage within the organ sections.

Anastomosis procedures are sometimes used to reattach the two ends of the organ sections after a cancerous portion of an organ has been resected. Medical studies have shown that the lack of certain types of bacteria are common in patients with colorectal cancer. As such, it is believed that patient microbiome is a factor in colorectal cancer recurrence. Fecal transplants have been successful in restoring gut microbiota to minimize the likelihood of adverse results that may occur after an anastomosis procedure has been performed.

A continuing need exists for a circular stapling device that can restore microbiota at an anastomotic site.

SUMMARY

This disclosure is directed to a circular stapling device for performing anastomoses. The stapling device includes an end effector that is adapted to deliver probiotics to an anastomotic site during formation of an anastomosis.

One aspect of the disclosure is directed to an anvil assembly including a head assembly, a center rod assembly, and probiotics. The head assembly includes a head housing, an anvil plate, and a cutting ring. The head housing defines an outer annular recess and an inner annular cavity. The anvil plate is secured within the outer annular recess and the cutting ring is supported within the inner annular cavity. The center rod assembly includes a center rod having a proximal portion, and a distal portion that is coupled to the head housing of the head assembly. The probiotics are supported on the anvil assembly.

Other aspects of the disclosure are directed to a surgical stapling device including an adapter assembly, an end effector, and probiotics. The adapter assembly has a proximal portion and a distal portion. The distal portion of the adapter assembly includes an anvil retainer that is movable between advanced and retracted positions. The end effector is supported adjacent the distal portion of the elongate body and includes a reload assembly and an anvil assembly. The reload assembly is supported on the distal portion of the elongate body and includes a shell housing, a pusher, and a staple cartridge including staples. The staple cartridge is supported on the shell housing, and the pusher is movable within the shell housing from a retracted position to an advanced position to eject the staples from the staple cartridge. The anvil assembly is releasably coupled to the anvil retainer and movable in relation to the staple cartridge between open and clamped positions in response to movement of the anvil retainer between its advanced and retracted positions. The anvil assembly includes a head assembly and a center rod assembly. The head assembly includes a head housing, an anvil plate, and a cutting ring. The head housing defines an outer annular recess and an inner annular cavity. The anvil plate is secured within the outer annular recess and the cutting ring is supported within the inner annular cavity. The center rod assembly includes a center rod having a proximal portion, and a distal portion that is coupled to the head housing of the head assembly. The probiotics are supported on the stapling device and are received within or deliverable to the end effector.

In aspects of the disclosure, the head housing includes a post that is centrally located within the inner annular cavity of the head housing, and the cutting ring is movable about the post within the inner annular cavity between retracted and advanced positions.

In some aspects of the disclosure, the head housing includes a distal inner wall that defines bores that extend through the head housing, and the probiotics are supported within a packet positioned between the cutting ring and the distal inner wall of the head housing.

In certain aspects of the disclosure, movement of the cutting ring from its retracted position towards its advanced position compresses the packet to dispense the probiotics from the packet through the bores in the head housing.

In aspects of the disclosure, a retainer member is positioned between the inner distal wall of the head housing and the cutting ring.

In some aspects of the disclosure, the retainer member includes deformable tabs and is positioned to retain the cutting ring in the retracted position until a predetermined force is applied to the cutting ring.

In certain aspects of the disclosure, the anvil assembly includes a container having the probiotics received within the container.

In aspects of the disclosure, the container is positioned within the inner annular cavity of the head housing between the inner distal wall of the head housing and the cutting ring such that movement of the cutting ring from its retracted position towards its advanced position compresses the container to dispense the probiotics from the container.

In some aspects of the disclosure, the container is formed from plastic or glass.

In aspects of the disclosure, a filter is positioned about the container and is configured to contain the container after the container has been compressed.

In certain aspects of the disclosure, the filter is formed from filter paper.

In aspects of the disclosure, the probiotics are supported within the inner annular cavity of the head housing, and the center rod supports a probiotic delivery system that includes a cylinder, a plunger, a delivery tube, and a gas bulb positioned within the cylinder.

In some aspects of the disclosure, the delivery tube communicates the cylinder with the inner annular cavity of the head housing, and the plunger is movable within the cylinder to deliver gas from the gas bulb to the inner annular cavity of the head housing to dispense the probiotics through the bores in the head housing.

In certain aspects of the disclosure, the probiotics are in powder form and are positioned between the inner distal wall of the head housing of the anvil assembly and the cutting ring.

In aspects of the disclosure, a sheet of material is positioned proximally of the probiotics between the cutting ring and the distal wall of the head housing to retain the probiotics within the head housing.

In some aspects of the disclosure, the sheet of material includes perforated slits.

In certain aspects of the disclosure, the anvil plate defines staple forming pockets and the probiotics are positioned within the staple forming pockets.

Other features of the disclosure will be appreciated from the following description.

BRIEF DESCRIPTION OF THE DRAWINGS

Various aspects of a circular stapling device are described herein below with reference to the drawings, wherein.

DETAILED DESCRIPTION

Figure 1:
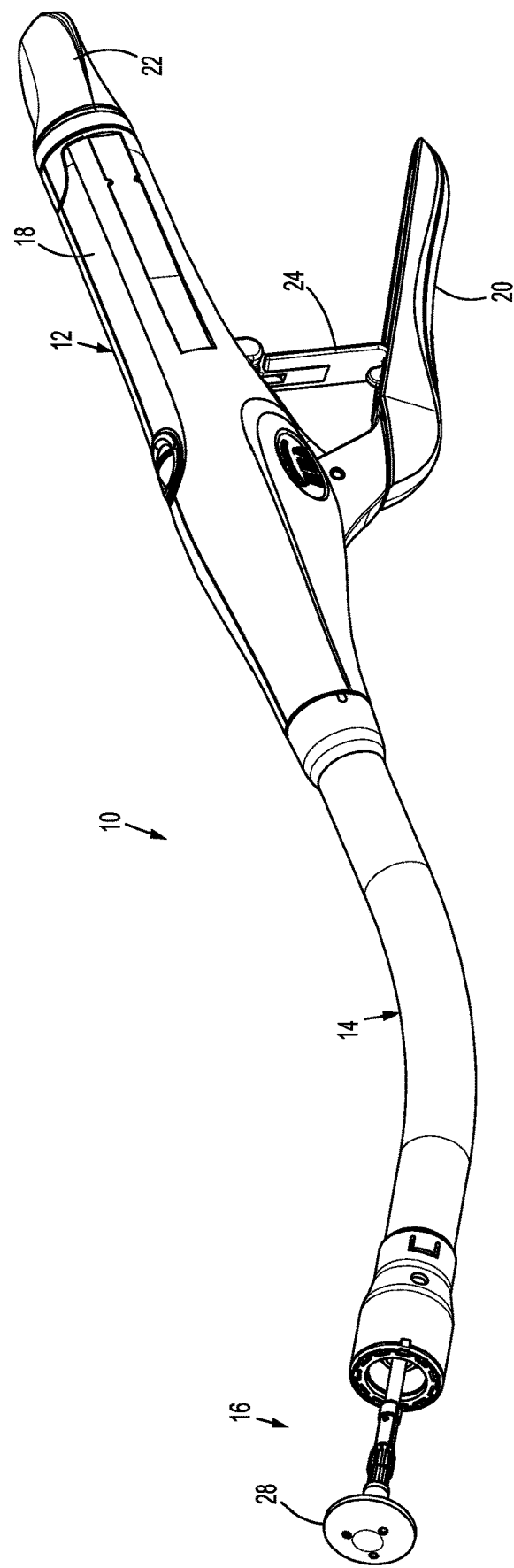
FIG. 1 is a perspective view of a circular stapling device according to aspects of the disclosure in an open position.

The disclosed surgical stapling device will now be described in detail with reference to the drawings in which like reference numerals designate identical or corresponding elements in each of the several views. However, it is to be understood that aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the stapling device in its customary manner, while the term "distal" is used generally to refer to that portion of the device that is farther from the clinician during use of the stapling device in its customary manner. In addition, the term "clinician" is used generally to refer to medical personnel including doctors, nurses, and support personnel. Further, directional terms such as front, rear, upper, lower, top, bottom, and similar terms are used to assist in understanding the description and are not intended to limit the disclosure.

This disclosure is directed to a circular stapling device that includes probiotics, i.e., live bacteria and yeasts that have health benefits, that can be delivered to an anastomotic site during formation of an anastomosis.

FIG. 1 illustrates a circular stapling device 10 shown generally as stapling device 10 that includes a handle assembly 12, an elongate body or adapter assembly 14 that extends distally from the handle assembly 12, and an end effector 16 that is coupled to a distal portion of the adapter assembly 14. The handle assembly 12 includes a stationary grip portion 18, a firing trigger 20, and an approximation knob 22. The handle assembly 12 also includes a firing lockout member 24 that is pivotally coupled to the stationary grip portion 18 and is movable from a locked position in which the lockout member 24 prevents actuation of the firing trigger 20 to an unlocked position in which the lockout member 24 permits actuation of the firing trigger 20. U.S. Pat. No. 10,022,126 discloses a circular stapling device that includes a handle assembly suitable for use with the circular stapling device described herein.

Although the circular stapling device is shown to include a manually actuated handle assembly, it is envisioned that the circular stapling device 10 could also include a powered handle assembly, or in the alternative, be adapted to for use with a robotic stapling system.

Figure 2:
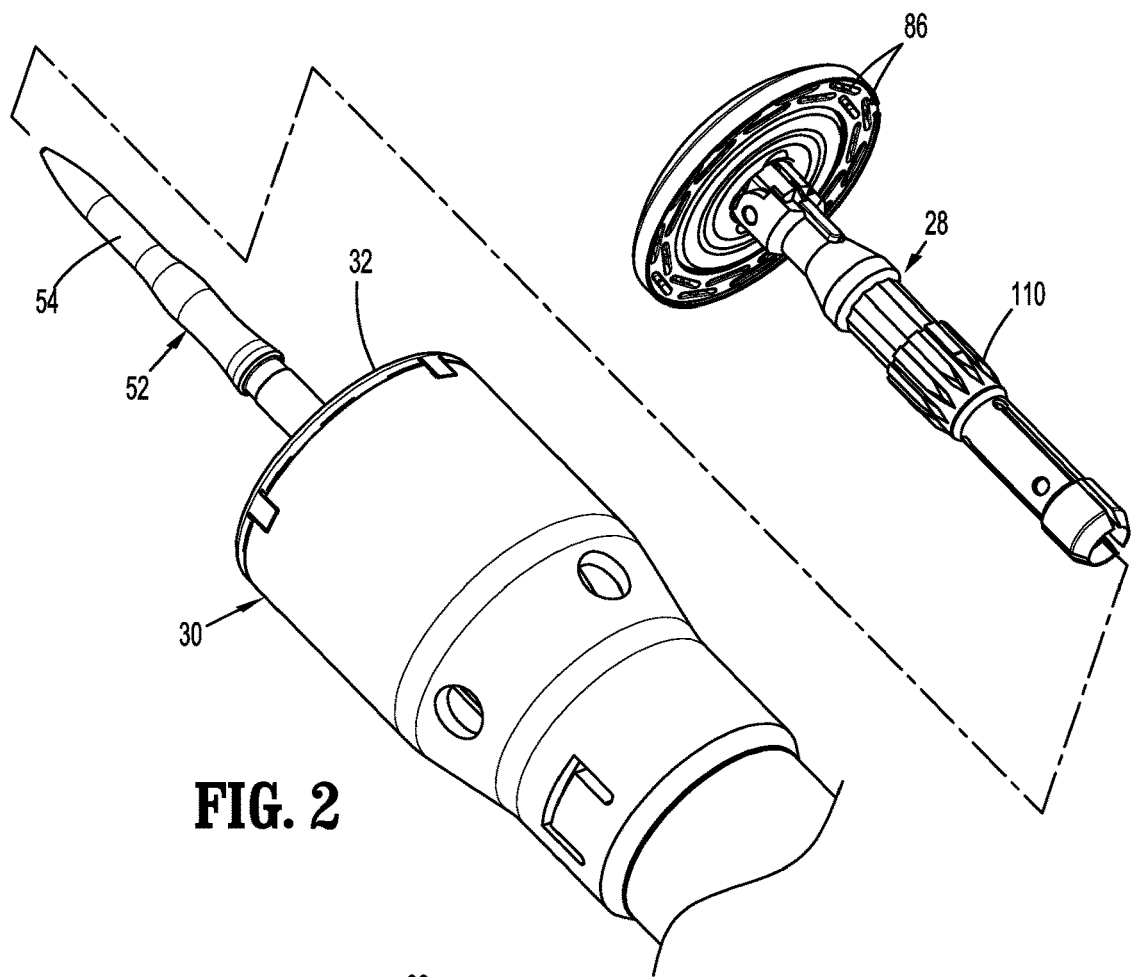
FIG. 2 is a side perspective view of a distal portion of the circular stapling device shown in FIG. 1 with an anvil assembly separated from an anvil retainer of the circular stapling device.
Figure 3:
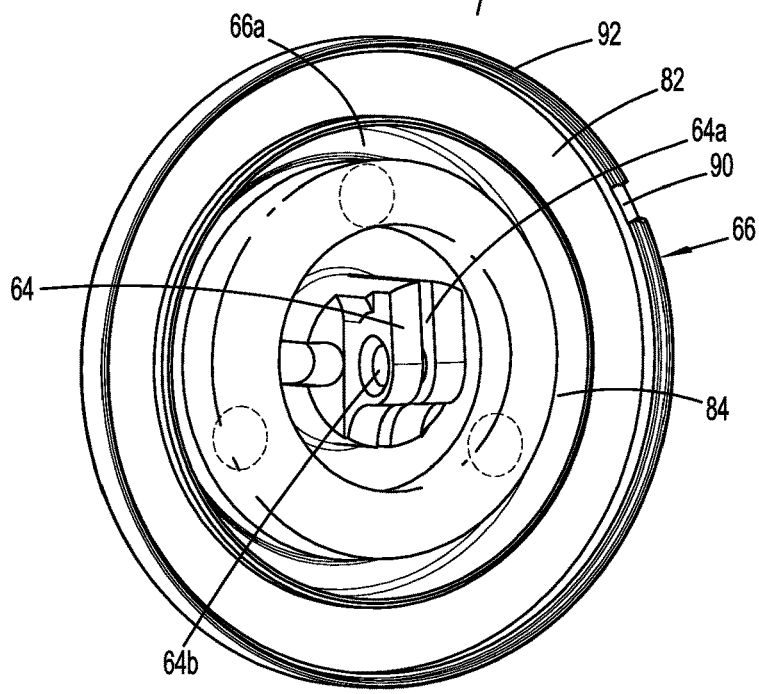
FIG. 3 is a perspective view from the proximal end of a housing of an anvil head assembly of the circular stapling device shown in FIG. 1.
Figure 8:
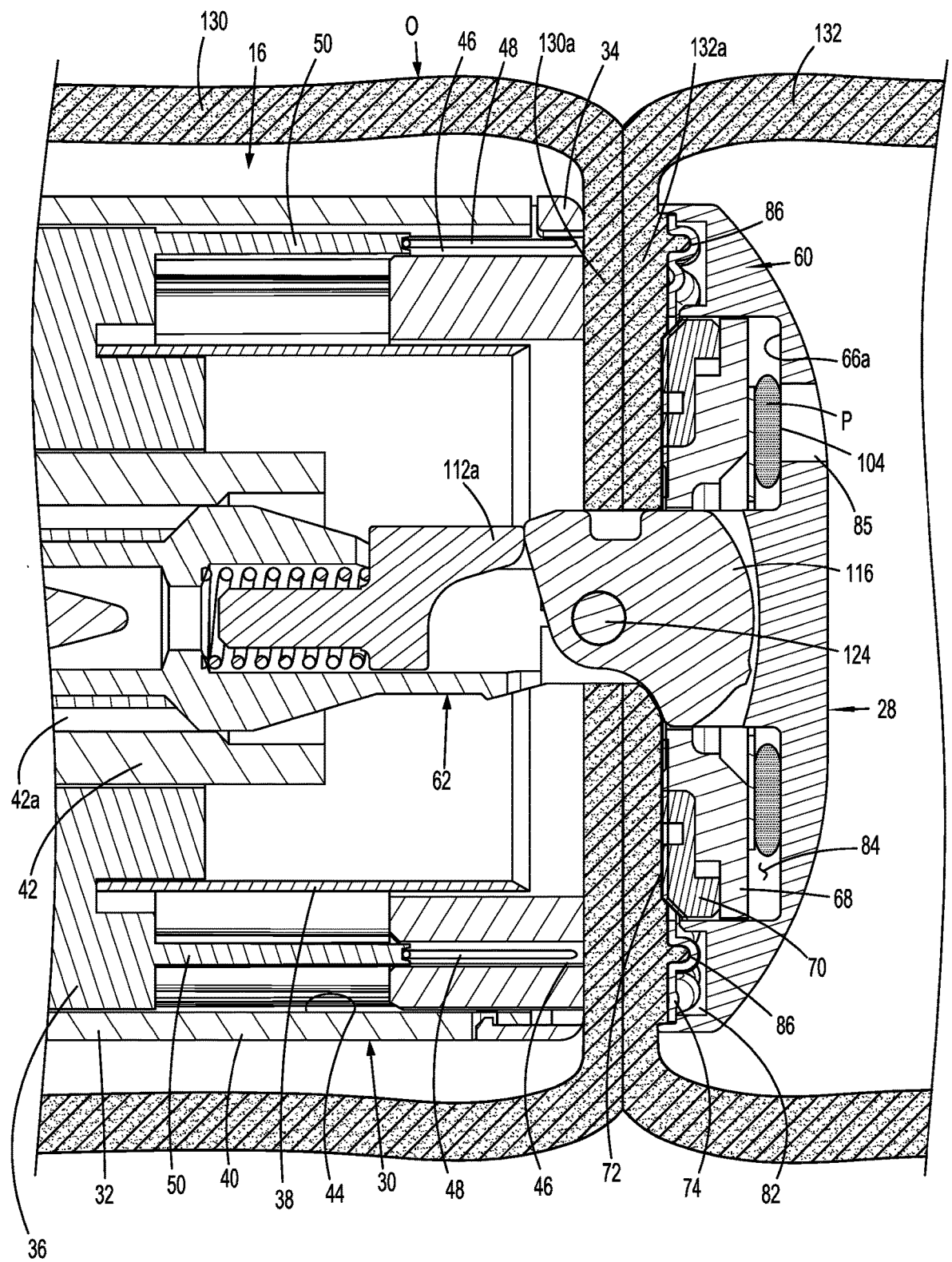
FIG. 8 is a cross-sectional view taken along section line 8-8 of FIG. 7.

FIGS. 2 and 8 illustrate the end effector 16 which includes an anvil assembly 28 and a reload assembly 30. The reload assembly 30 includes a shell housing 32, a staple cartridge 34, an annular pusher 36, and an annular knife 38. The shell housing 32 includes an outer housing portion 40 and an inner housing portion 42 that together define an annular cavity 44 (FIG. 8). The inner housing portion 42 defines a through bore 42a (FIG. 8). The pusher 36 is received within the annular cavity 44 and is movable between retracted and advanced positions in response to actuation of the firing trigger 20. The annular knife 38 is supported on a distal portion of the pusher 36 and is movable with the pusher 36 to cut tissue clamped between the anvil assembly 28 and the staple cartridge 34. Alternately, such as in some powered stapling devices, the annular knife 38 can be movable independently of the pusher 36. The staple cartridge 34 defines staple receiving slots 46 (FIG. 8) that receive staples 48 and fingers 50 of the pusher 36. When the pusher 36 is moved from its retracted position towards it advanced position, the fingers 50 move through the staple receiving slots 46 of the staple cartridge 34 to eject the staples 48 from the staple cartridge 34.

The adapter assembly 14 (FIG. 1) includes an anvil retainer 52 that is configured to be releasably coupled to the anvil assembly 28. The anvil retainer 52 extends through the through bore 42a of the inner housing portion 42 of the shell housing 32 and includes a distal portion that defines a trocar 54 that extends from a distal end of the shell housing 32. The anvil retainer 52 is movable from an advanced position to a retracted position to move the anvil assembly 28 in relation to the staple cartridge 34 between open and clamped positions.

FIGS. 3-6 illustrate the anvil assembly 28 of the surgical stapling device 10 (FIG. 1) which includes a head assembly 60 and a center rod assembly 62. The head assembly 60 includes a post 64 (FIG. 3), a head housing 66, a backup member 68, a cutting ring 70, a cutting ring cover 72, an anvil plate 74, and a retainer member 80. The post 64 defines a longitudinal slot 64a and a transverse bore 64b. The head housing 66 defines an outer annular recess 82, an inner annular cavity 84 formed about the post 64, and bores 85 that extend through the head housing 66 and communicate with the inner annular cavity 84. The post 64 is centrally located within the inner cavity 84 of the head housing 66. In aspects of the disclosure, the post 64 is formed separately from the head housing 66 and is secured to the head housing 66 by welding or crimping. Alternately, it is envisioned that the post 64 could be monolithically formed with the head housing 66.

The anvil plate 74 has an annular configuration and is supported in the outer annular recess 82 (FIG. 3) of the head housing 66 about the inner cavity 84. The anvil plate 74 defines a plurality of staple forming pockets 86 (FIG. 2) and includes a tab 88. The staple forming pockets 86 receive and form the staples 48 when the stapling device 10 (FIG. 1) is fired. The tab 88 extends radially outwardly from the anvil plate 74 and is received within a cutout 90 (FIG. 3) formed in an outer rim 92 of the head housing 66. Receipt of the tab 88 within the cutout 90 functions to align the anvil plate 74 with the staple cartridge 32 such that the staples 48 are properly received within the staple forming pockets 86 of the anvil plate 74.

The backup member 68 defines a central opening 68a that is positioned about the post 66 within the inner annular cavity 84 of the head housing 66 between the post 64 and the outer annular recess 82. The backup member 68 includes a raised, distally extending platform 96 and an annular body 98 that defines cutouts 100. The raised platform 96 includes fingers 96a that extend radially inwardly from the raised platform 96. The cutting ring 70 has an annular configuration and defines a central opening 70a that has a configuration that corresponds to the configuration of the raised platform 96 of the backup member 68. The raised platform 96 is received within the central opening 70a of the cutting ring 70 to secure the cutting ring 70 to the backup member 68. Although the platform 96 and the central opening 70a of the cutting ring 70 are illustrated as having a circular shape, other configurations are envisioned, e.g., square, rectangular, triangular, etc. In certain aspects of the disclosure, the cutouts 100 in the annular body 98 of the backup member 68 receives protrusions 78 formed on the cutting ring 70 to frictionally secure the cutting ring 70 to the backup member 68.

Figure 6:
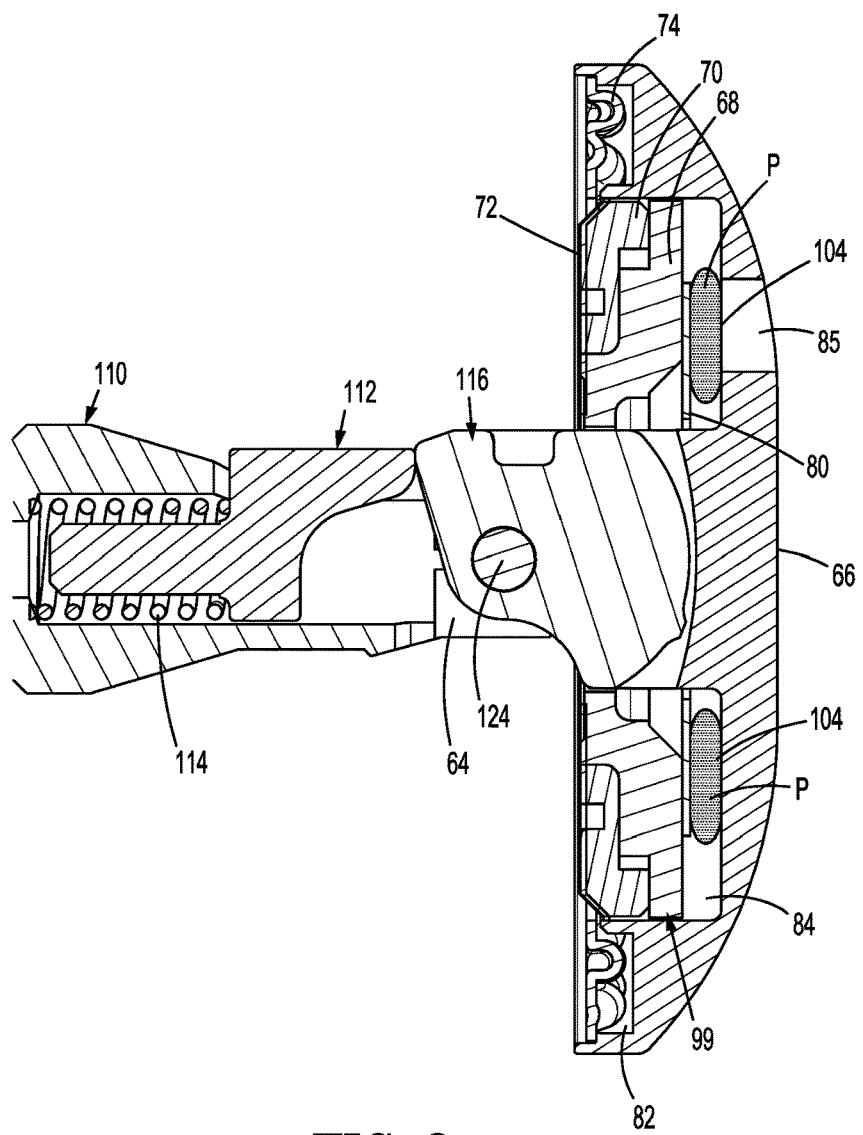
FIG. 6 is a cross-sectional view taken along section line 6-6 of FIG. 5.

In aspects of the disclosure, the cutting ring 70 is formed from polyethylene and is fixedly secured to the backup member 68 using, for example, friction fitting or adhesives, to form a backup member/cutting ring assembly 99 (FIG. 6). The backup member 68 is formed from a hard material, e.g., a metal. Alternately other materials of construction may be used to construct the backup plate 68 and the cutting ring 70.

The cutting ring cover 72 defines a central opening 72a and is secured about the post 64 of the head housing 66 to a proximal surface of the cutting ring 70 using, for example, an adhesive. In aspects of the disclosure, the cutting ring cover 72 is formed from a material or materials, having hardness greater than that of the cutting ring, e.g., mylar. In some aspects of the disclosure, the cutting ring cover 72 includes two layers of mylar which are joined together using an adhesive, and a polypropylene coating. Alternately, the cutting ring 70 need not have a cover 72. The cutting ring 70, the backup member 68, and the cover 72 form the backup member/cutting ring assembly 99 which is slidably mounted about the post 64 as a single construct from a retracted position to an advanced position in response to firing of the stapling device 10 as described below.

The retainer member 80 is positioned within the inner annular cavity 84 of the head housing 66 between the backup member 68 and a distal inner wall 66a (FIG. 3) of the head housing 66. In aspects of the disclosure, the retainer member 80 has an annular configuration and defines an opening 80a that receives the post 64. In some aspects of the disclosure, the retainer member 80 includes a plurality of deformable tabs 102 which engage the distal wall 66a of the head housing 66 to prevent the backup member/cutting ring assembly 99 from moving within the inner annular cavity 84 from the retracted position to the advanced position until a predetermined force sufficient to deform the tabs 102 has been applied to the backup plate/cutting ring assembly 99. The predetermined force can be close to but is less than the force applied by the annular knife 38 of the stapling device 10 on the cutting ring 70 when stapling device 10 is fired. In aspects of the disclosure, the predetermined force is between about ten pounds and about ninety pounds and can be about thirty (30) pounds. When the predetermined force is reached, the tabs 102 of the retainer member 80 deform and the backup member/cutting ring assembly 99 is urged into the inner annular cavity 84 from its retracted position to its advanced position. It is envisioned that other crushable, deformable, collapsible or movement restricting retaining members may be used to retain the backup plate/cutting ring assembly 99 in a fixed retracted position within the inner annular cavity 84 of the head housing 66 until the predetermined force has been applied to the backup plate/cutting ring assembly 99.

The head assembly 60 of the anvil assembly 28 also includes a packet 104 that is filled with probiotics P (FIG. 6) and is positioned between a distal face 80b (FIG. 4) of the retainer member 80 and the distal wall 66a of the head housing 66a. When the head assembly 60 is assembled, the tabs 102 are positioned radially outward of the packet 104 and confine the packet 104 within the retainer member 80. In aspects of the disclosure, the probiotics P are in liquid or gel form. When the backup member/cutting ring assembly 99 is moved from its retracted to its advanced position and the tabs 102 of the retainer member 80 are deformed, the packet 104 is compressed and collapses or breaks to expel the probiotics P from the packet 104 through the bores 85 in the head housing 66. When the probiotics P are expelled from the packet 104 through the bores 85 in the head housing 66, the probiotics P are dispensed onto tissue at that anastomotic site. In aspects of the disclosure, the packet 104 is formed of collagen although other materials of construction are envisioned.

Figure 4:
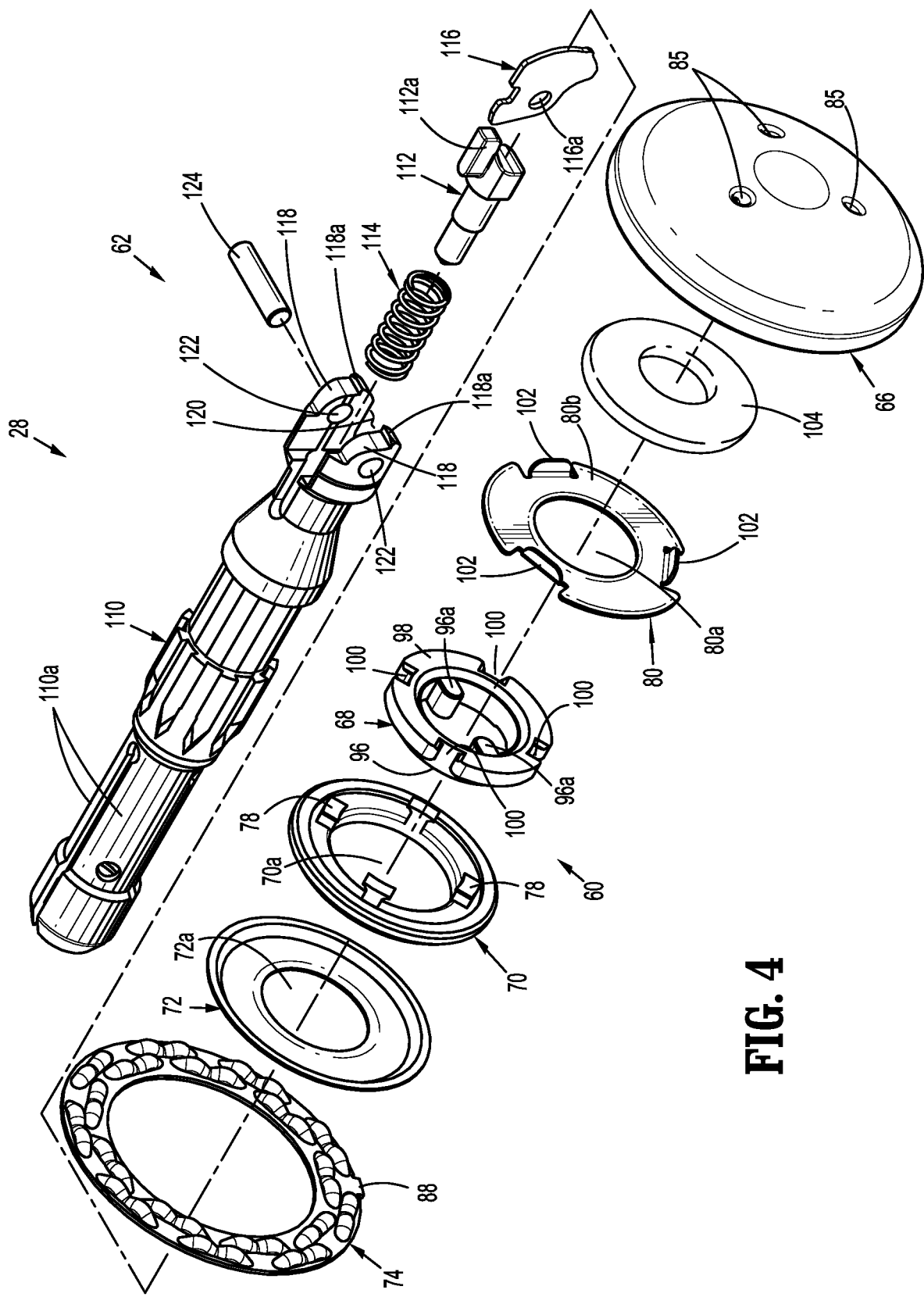
FIG. 4 is a side perspective exploded view of the anvil assembly shown in FIG. 2.
Figure 5:
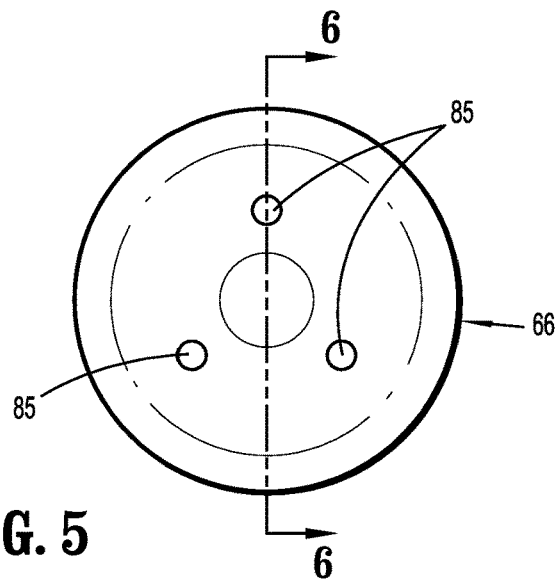
FIG. 5 is a perspective view from the distal end of the anvil head assembly shown in FIG. 3.

FIGS. 2, 4, and 6 illustrate the anvil center rod assembly 62 which includes a center rod 110, a plunger 112, a plunger spring 114, and a cam latch member 116. The center rod 110 has a distal end that includes two arms 118 that are spaced from each other to define a cavity 120 (FIG. 4). Each arm 118 includes a stop surface 118a and defines a through bore 122 that is substantially perpendicular to a central longitudinal axis of the center rod 110. The post 64 of the head housing 66 is received within the cavity 120 such that the transverse bore 64b of the post 64 is aligned with the through bores 122 of the arms 118. A pivot member 124 is received within the transverse bore 64b and the through bores 122 to pivotally secure the post 64 to the center rod 110 such that the head assembly 60 is pivotally mounted to the anvil center rod assembly 62. A proximal portion of the center rod 110 includes a plurality of flexible legs 110a (FIG. 4) that define a bore (not shown) that receives the anvil retainer 52 of the stapling device 10 (FIG. 2) to releasably couple the anvil assembly 28 to the anvil retainer 52.

The distal end of the center rod 110 defines a cavity 126 (FIG. 6) that receives the plunger 112 and the plunger spring 114. The plunger spring 114 is positioned to urge the plunger 112 in a distal direction towards the head assembly 60. The plunger 112 includes a distal finger 112a that engages the cam latch member 116 and the post 64 at a position offset from a longitudinal axis of the center rod 110 to urge the head assembly 60 in relation to the center rod assembly 62 from an operative position (FIG. 6) towards a tilted position (not shown).

The cam latch member 116 is received within the longitudinal slot 64a of the post 64 and includes a body that defines a through bore 116a that receives the pivot member 124 such that the cam latch member 116 is pivotal within the longitudinal slot 64a of the post 64 of the head housing 66 of the head assembly 60. The cam latch member 116 includes a body that has an outer geometry that increases a contact force between the cam latch member 116 and an inner surface of the backup member 68 as the cam latch member 116 is rotated by the plunger 112 to prevent proximal movement of the backup member/cutting ring assembly 99 when the anvil assembly 28 is moved from its retracted position back to its advanced position after the stapling device 10 has been fired. Operation of the cam latch member 116 is known in the art and is not described in further detail herein.

FIG. 6 illustrates a distal portion of the anvil assembly 28 in a pre-fired position. In the pre-fired position, the backup plate/cutting ring assembly 99 is in the retracted position about the post 64 within the inner annular cavity 84 of the head housing 66. When the backup member/cutting ring assembly 99 is in a retracted position, the fingers 96a of the backup member 68 are positioned on a distal face of the arms 118 of the center rod 110 with the stop surfaces 118a of the arms 118 of the center rod 110 engaged with the fingers 96a (FIG. 4) of the backup member 68. In this position, the head assembly 60 of the anvil assembly 28 is retained in its operative position in relation to the center rod assembly 62 and cannot pivot towards its tilted position.

Figure 7:
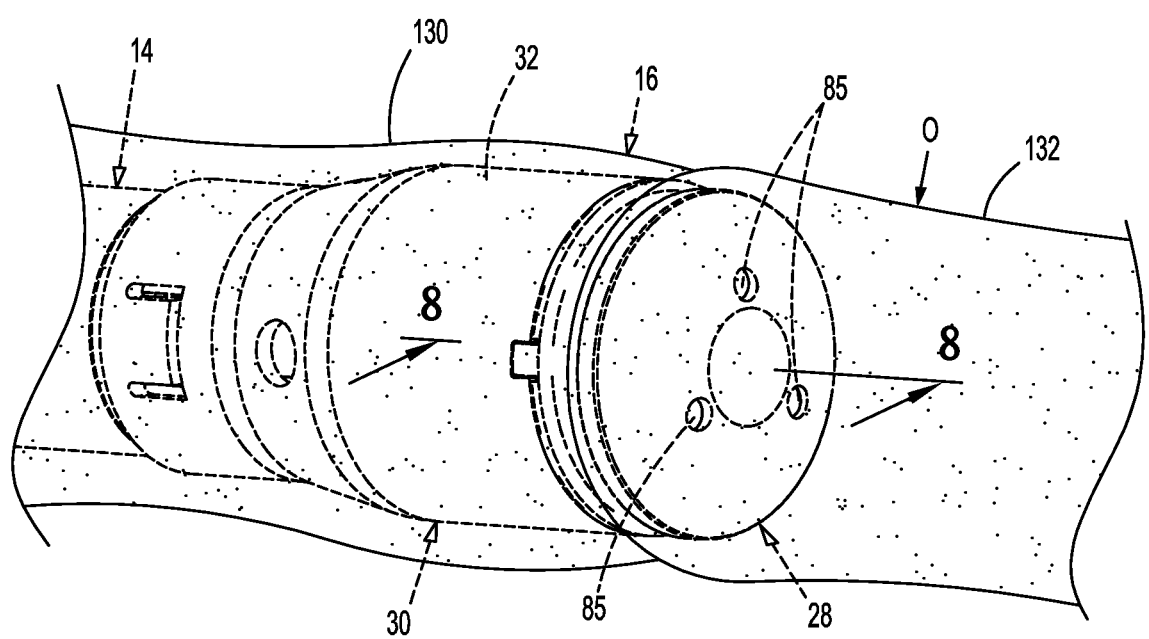
FIG. 7 is a side cutaway view of the distal portion of the circular stapling device shown in FIG. 1 shown in phantom and positioned within a body organ in a clamped position.

FIGS. 7 and 8 illustrate the distal portion of the stapling device 10 positioned within organ sections 130 and 132 of an organ "O", e.g., a colon, of a patient with the anvil assembly 28 in the clamped, pre-fired position and end sections 130a and 132a of the organ sections 130 and 132 clamped between the head assembly 60 of the anvil assembly 28 and the staple cartridge 34. In this position, the backup member/cutting ring assembly 99 is in its retracted position and the packet 104 is intact with the probiotics "P" confined within the packet 104.

Figure 9:
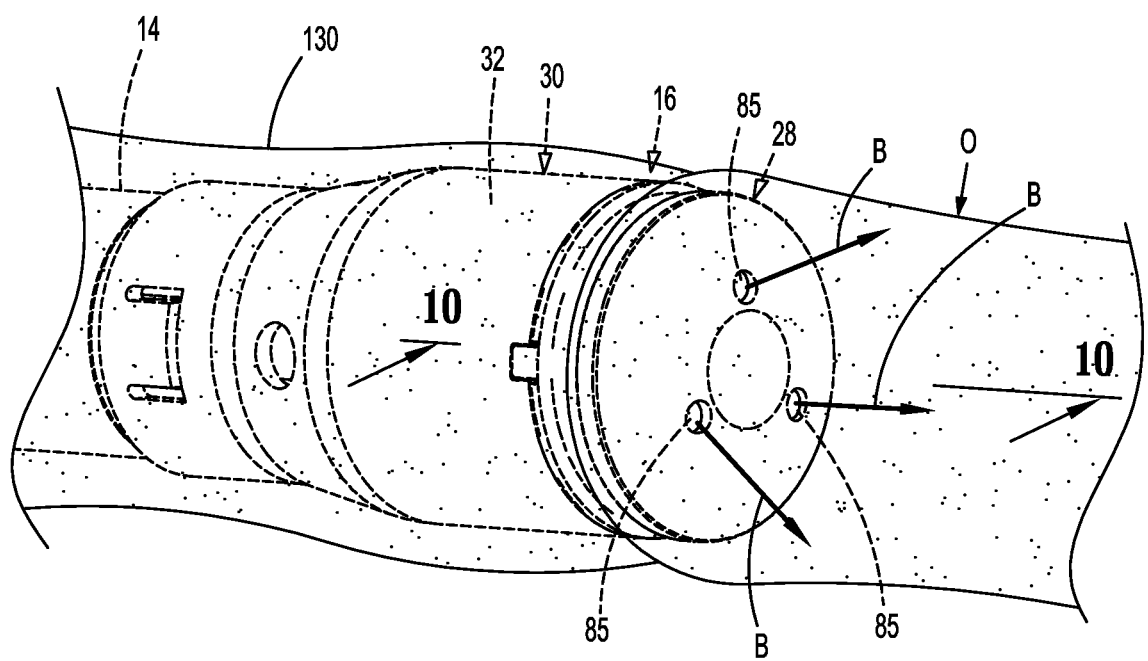
FIG. 9 is a side cutaway view of the distal portion of the circular stapling device shown in FIG. 1 shown in phantom and positioned within the body organ in a fired position.
Figure 10:
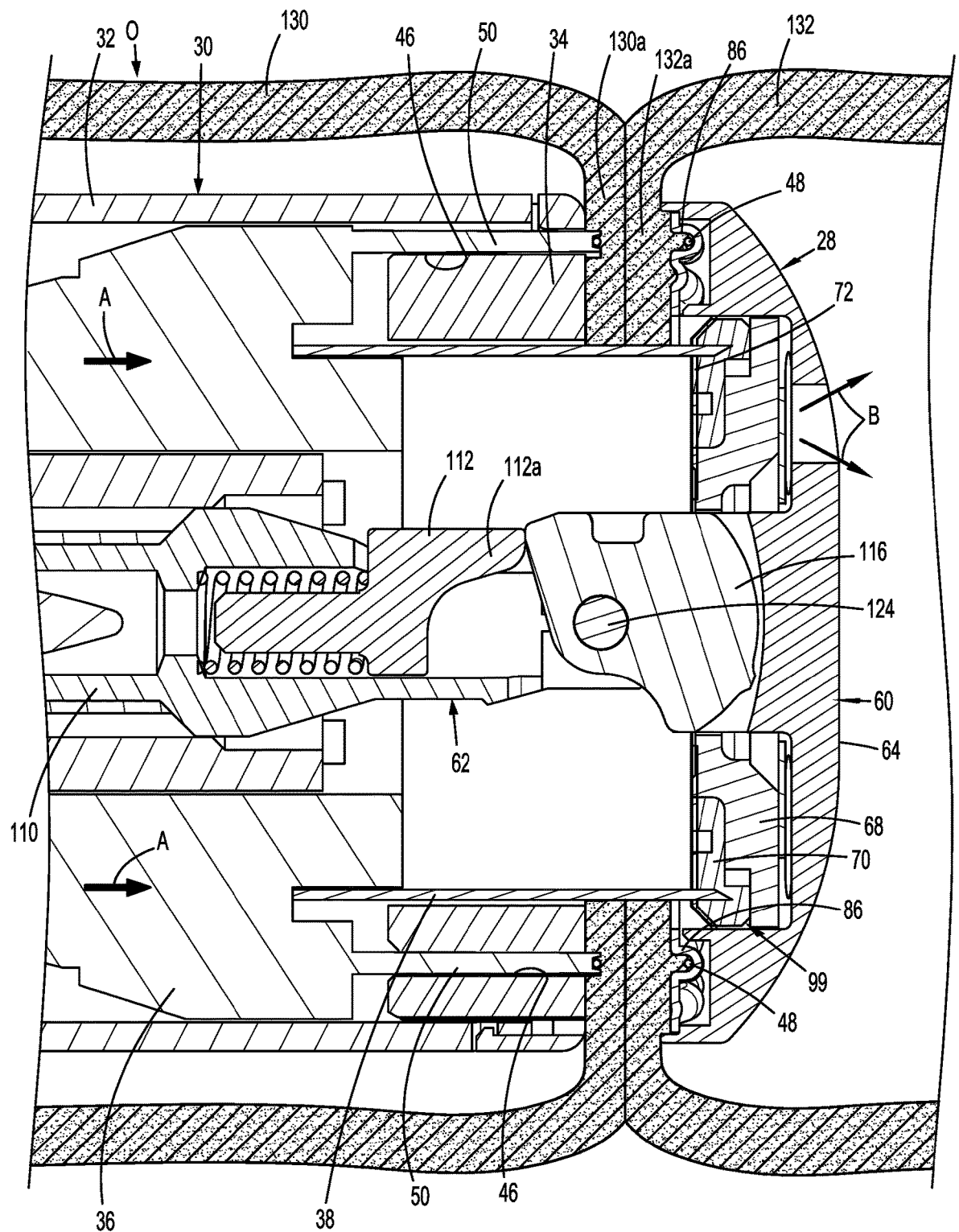
FIG. 10 is a cross-sectional view taken along section line 10-10 of FIG. 9.
Figure 11:
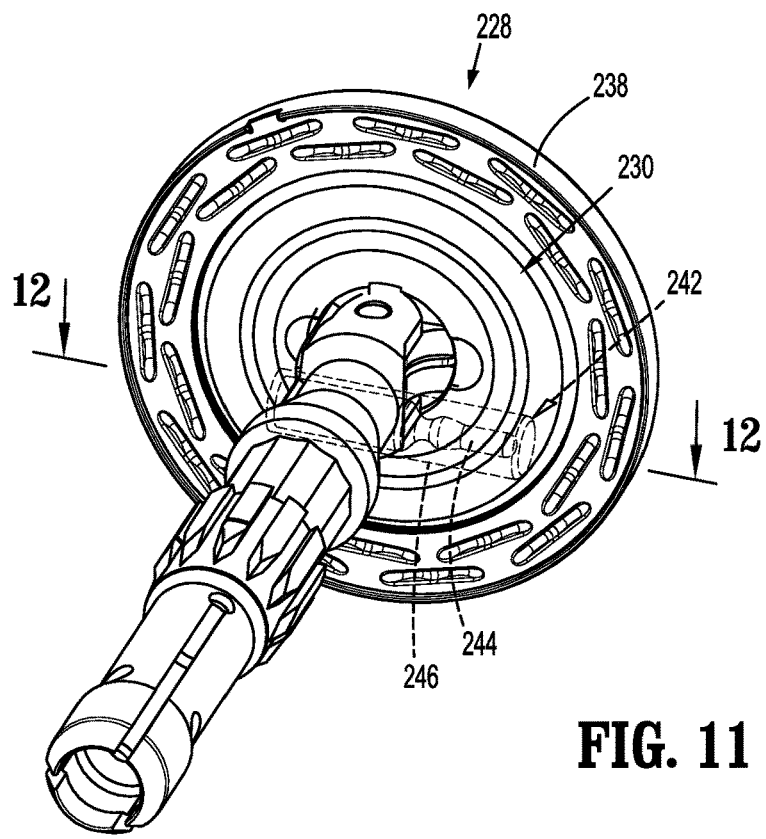
FIG. 11 illustrates a perspective view from the proximal end of an alternate version of the anvil assembly of the circular stapling device shown in FIG. 1.
Figure 12:
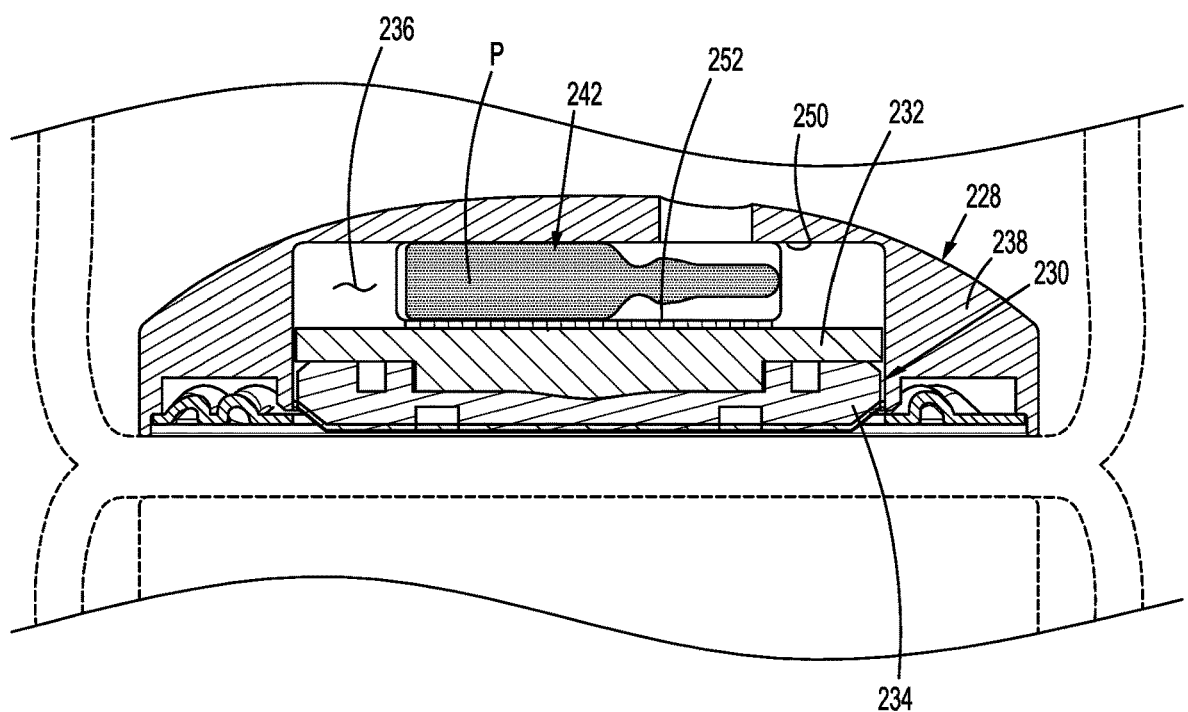
FIG. 12 is a cross-sectional view taken along section line 12-12 of FIG. 11.
Figure 13:
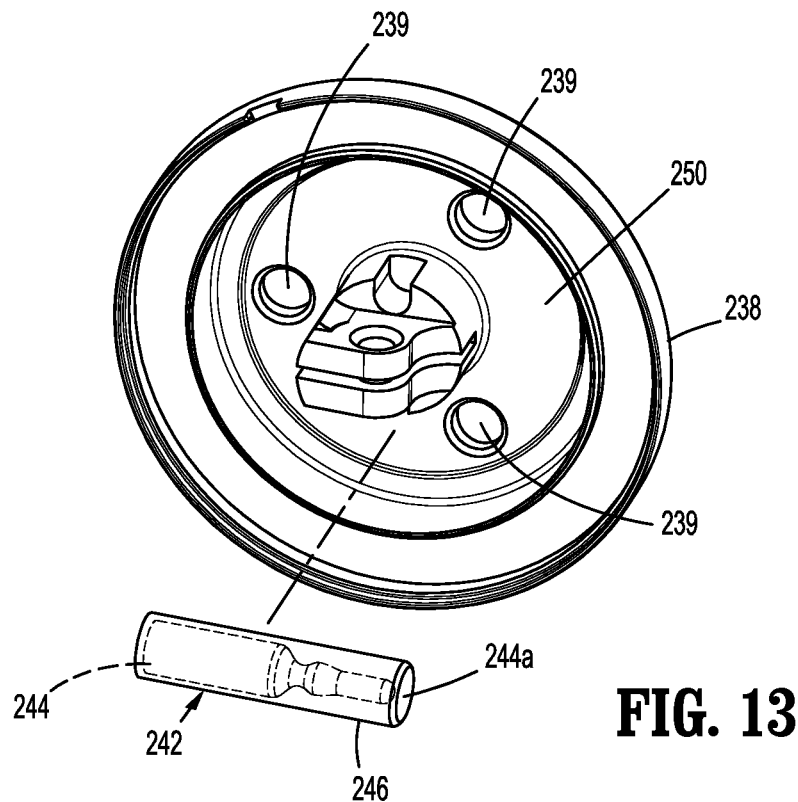
FIG. 13 is a perspective view from the proximal end of a housing of the anvil head assembly of the anvil assembly shown in FIG. 11 with a probiotics container assembly separated from the housing.
Figure 14:
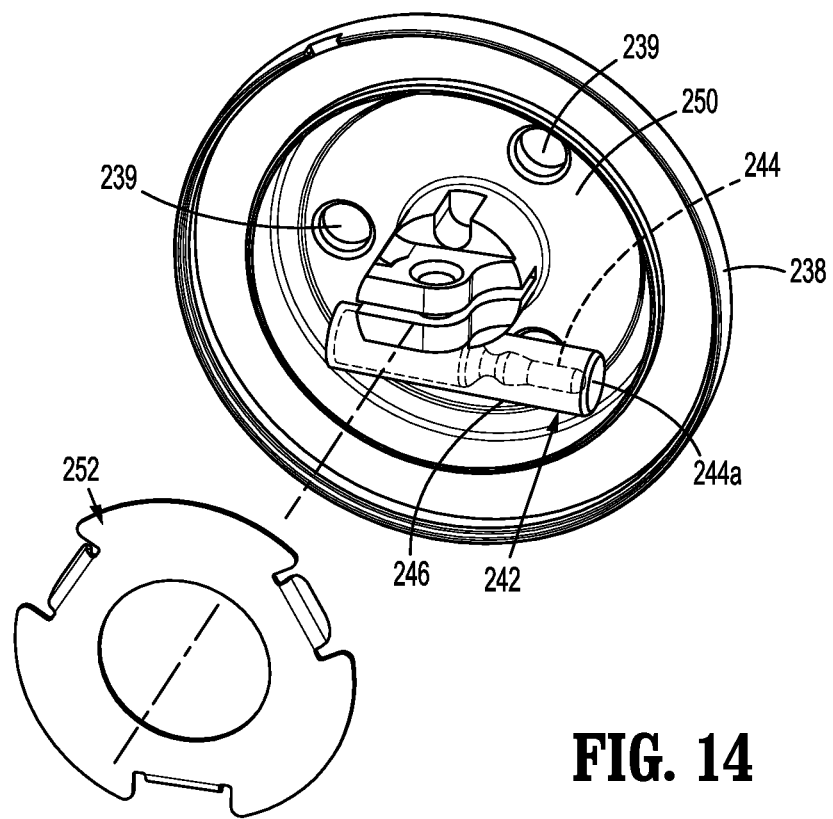
FIG. 14 is a perspective view from the proximal end of a housing of the anvil head assembly of the anvil assembly shown in FIG. 11 with a probiotics container assembly positioned in the housing and a crush plate separated from the housing.
Figure 15:
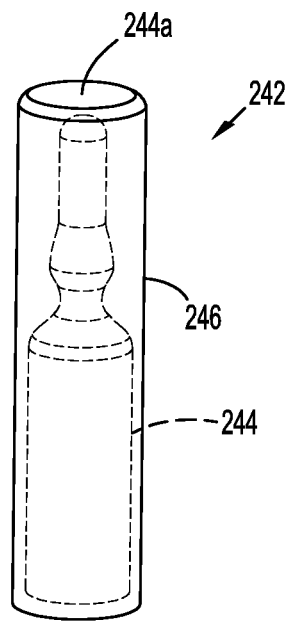
FIG. 15 is a side perspective view of the probiotics container assembly shown in FIG. 13 with a probiotics container shown in phantom.
Figure 16:
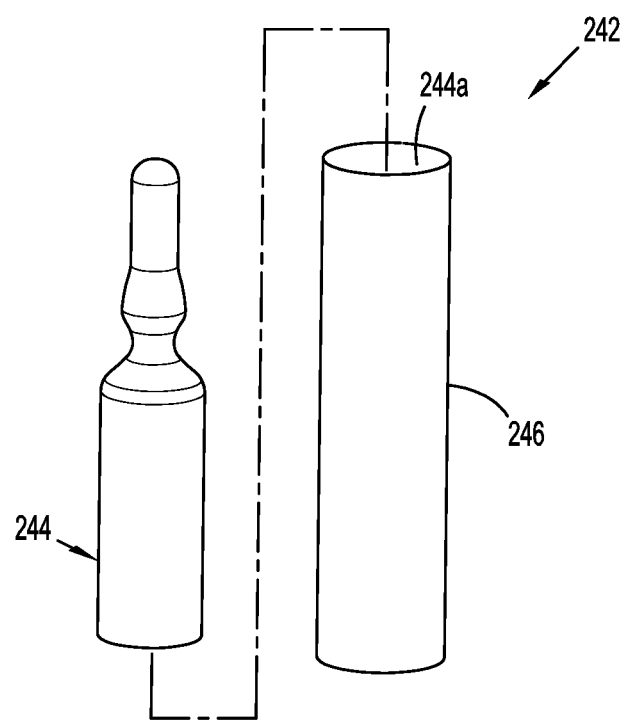
FIG. 16 is a side perspective view of the probiotics container assembly shown in FIG. 15 with the probiotics container removed from a liner of the probiotics container assembly.

FIGS. 9 and 10 illustrate the distal portion of the stapling device 10 positioned within the organ sections 130 and 132 of the organ "O" of a patient with the anvil assembly 28 in the clamped and fired position and the end sections 130a and 132a of the organ sections 130 and 132 secured together by the staples 48. When the pusher 36 is moved from its retracted position towards its advanced position in the direction indicated by arrows "A" in FIG. 10, the fingers 50 of the pusher 36 translate through the staple receiving slots 46 of the staple cartridge 34 to eject the staples 48 into the staple forming pockets 86 of the anvil plate 74. Concurrently, the annular knife 38 is advanced in the direction indicated by arrows "A" into engagement with the cutting ring 70 to deform the tabs 102 (FIG. 80) of the retainer member 80 and advance the backup member/cutting ring assembly 99 within the inner annular cavity 84 of the head housing 64 about the post 64 from its retracted position to its advanced position. When the backup member/cutting ring assembly 99 moves to its advanced position, the packet 104 is compressed and bursts or fractures to expel the probiotics "P" from the packet 104 through the bores 85 in the head housing 66 in the directions indicated by arrows "B" onto tissue at the anastomotic site.

FIGS. 11-16 illustrate and alternative version of the anvil assembly of the stapling device 10 shown generally as anvil assembly 228. The anvil assembly 228 is substantially similar to the anvil assembly 28 (FIG. 6) and includes a backup member/cutting ring assembly 230. The backup member/cutting ring assembly 230 includes a backup member 232 and a cutting ring 234 and is movable within an inner annular cavity 236 of a head housing 238 of a head assembly 240 of the anvil assembly 228 between retracted and advanced positions. The head housing 238 defines bores 239. The anvil assembly 228 differs from the anvil assembly 28 in that the packet 104 of probiotics "P" is replaced by a probiotics ampoule or container assembly 242.

The probiotics container assembly 242 includes a body 244 and a filter 246 that is positioned about or adjacent the body 244. The body 244 is formed from glass or plastic and defines a cavity 244a that receives probiotics "P" (FIG. 12) that are in liquid or gel form. In aspects of the disclosure, the body 244 can have a variety of configurations suitable for the intended purpose described below. The probiotics container assembly 242 is positioned between a distal inner wall 250 of the head housing 238 and a retainer member 252 of the anvil head assembly 240. The retainer member 252 is substantially similar to the retainer member 80 (FIG. 4) of the anvil assembly 28 and will not be described further herein.

Figure 17:
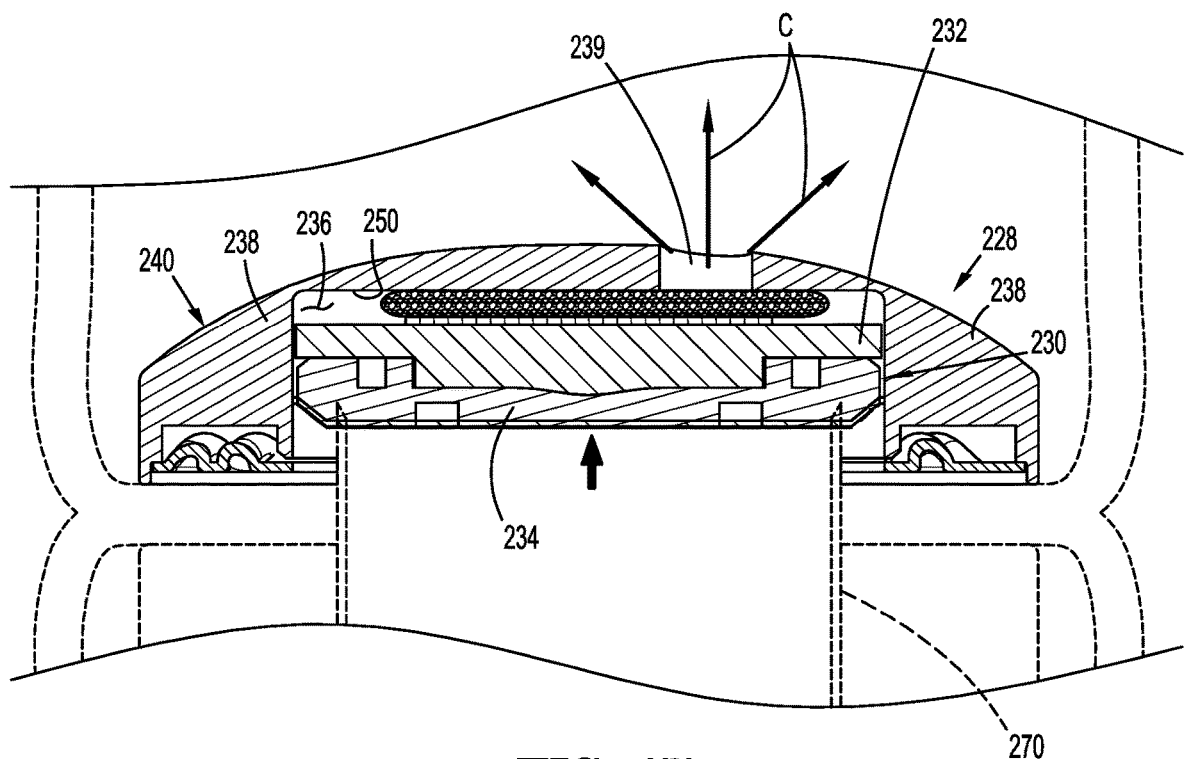
FIG. 17 is a cross-sectional view taken through the anvil assembly shown in FIG. 11 with the anvil positioned within an organ of a patient shown in phantom as the circular stapling device shown in FIG. 1 is fired.
Figure 18:
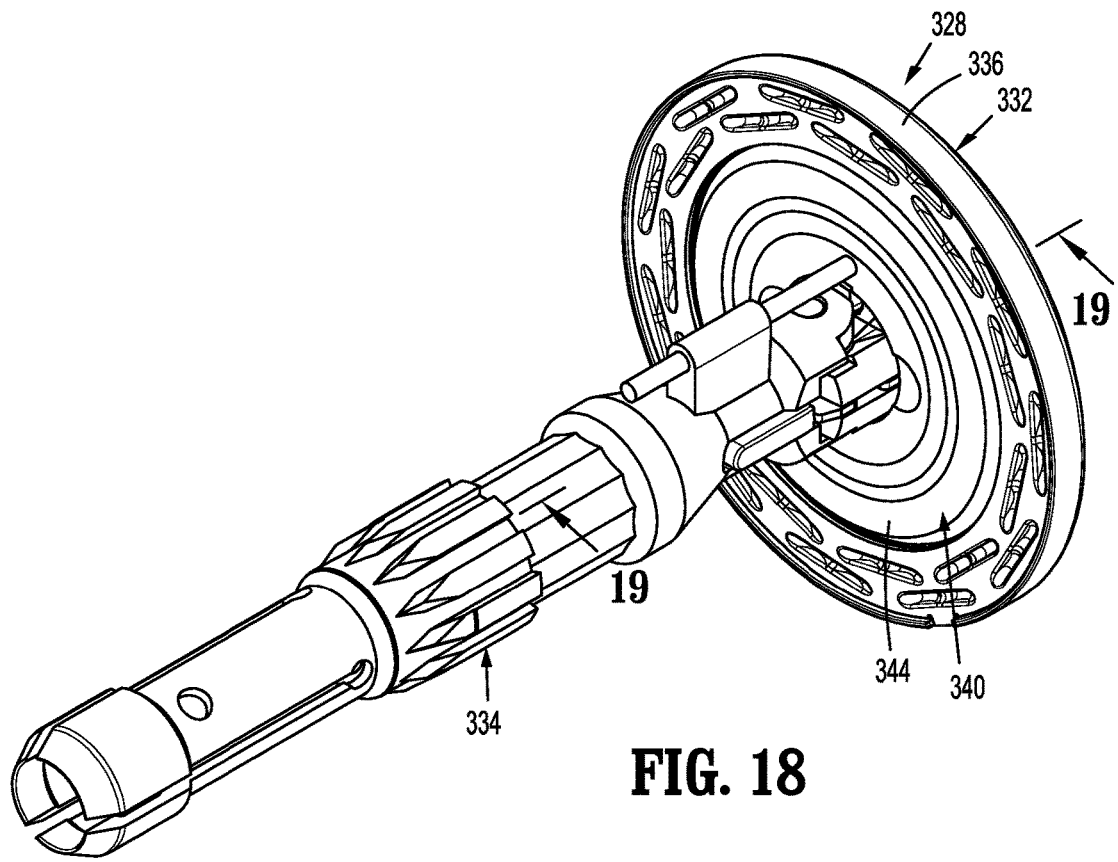
FIG. 18 is another version of the anvil assembly of the circular stapling device shown in FIG. 1.
Figure 19:
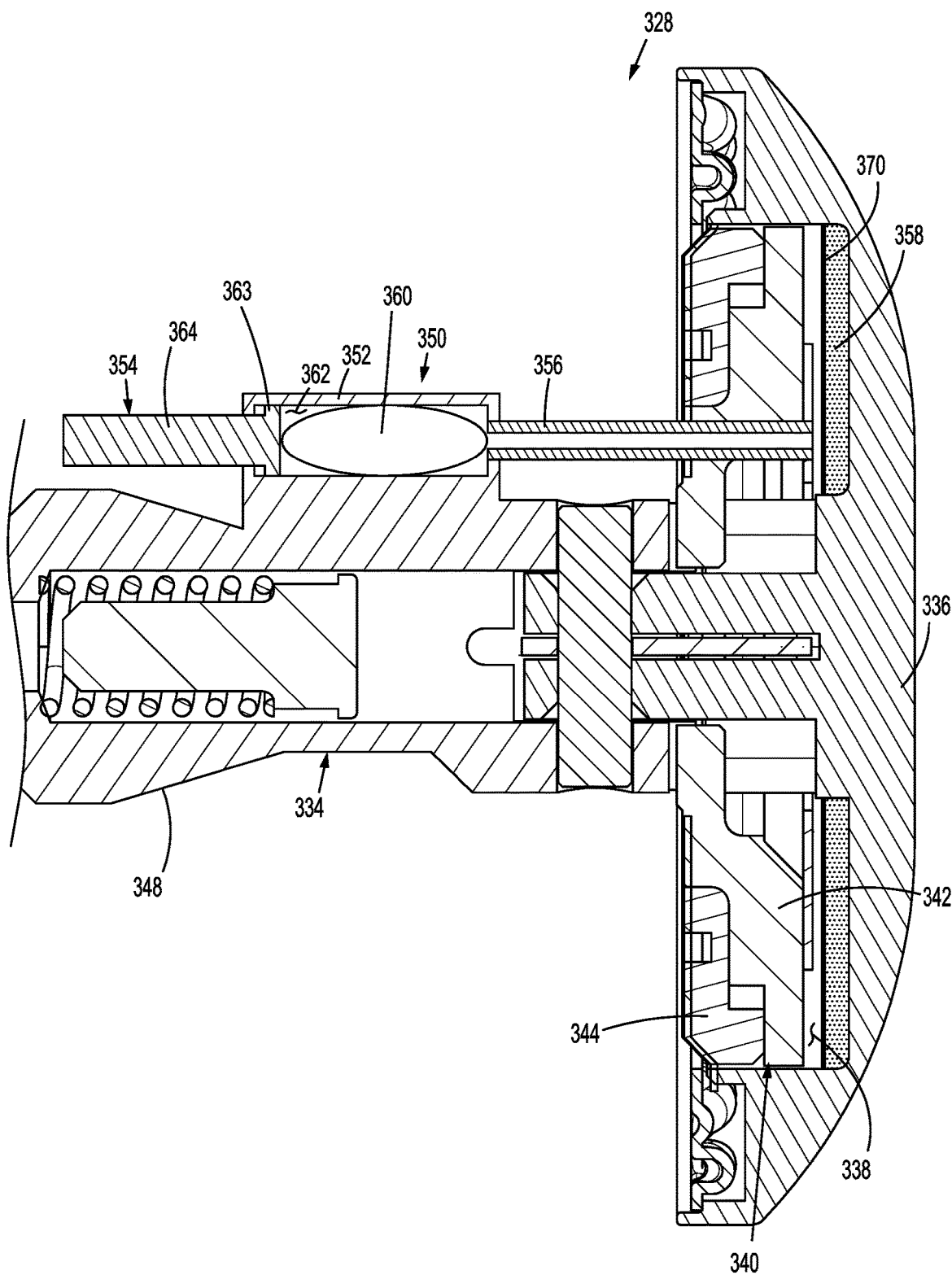
FIG. 19 is a cross-sectional view taken along section line 19-19 of FIG. 18.

The anvil assembly 228 functions in a manner similar to the anvil assembly 28 described above. More specifically, as shown in FIG. 17, when the backup member/cutting ring assembly 230 moves to its advanced position in response to advancement of an annular knife 270 and firing of the stapling device 10 (FIG. 1) as described above, the probiotics container assembly 242 is compressed between the retainer member 252 and the distal inner wall 250 of the head housing 238 and fractures or bursts to expel the probiotics "P" from the body 244 through the bores 239 in the head housing 238 in the direction of arrows "C" onto tissue at the anastomotic site. In some aspects of the disclosure, the filter 246 is formed from filter paper and is positioned or wrapped about the body 244. Alternately, the filter 246 need not be positioned about the body 244 but can be positioned between the body 244 and the bores 239 in the head housing 238.

FIGS. 18-26 illustrate another alternate version of the anvil assembly of the stapling device of FIG. 1 shown generally as anvil assembly 328. The anvil assembly 328 is substantially similar to the anvil assembly 28 (FIG. 6) and includes a head assembly 332 and a center rod assembly 334. The head assembly 332 includes a head housing 336 that defines an inner annular cavity 338 and a backup member/cutting ring assembly 340. The backup member/cutting ring assembly 340 includes a backup member 342 and a cutting ring 344 that is secured to the backup member 342 such that the backup member/cutting ring assembly 340 is movable within the inner annular cavity 338 of the head housing 336 of the head assembly 340 of the anvil assembly 328 between retracted and advanced positions. As described above regarding the anvil assemblies 28 and 228, the head housing 336 defines bores 346 that communicate with the inner annular cavity 338. The center rod assembly 334 is substantially similar to the center rod assembly 62 (FIG. 4) described above and includes a center rod 348.

The anvil assembly 328 differs from the anvil assemblies 28 and 228 described above in that the anvil assembly 328 includes a probiotics delivery system 350 including a cylinder 352, a plunger 354, a delivery tube 356, probiotics powder "P", and a gas filled bulb 360. The cylinder 352 is fixedly secured to the center rod 348 and defines a cavity 362 that receives the gas filled bulb 360. The cylinder 352 includes an open distal end that receives a proximal portion of the delivery tube 356 and an open proximal end that receives the plunger 354. The plunger 354 includes a plunger head 363 that is slidably received within the cavity 362 of the cylinder 352 and a plunger shaft 364 that extends through the open proximal end of the cylinder 352. The delivery tube 356 connects the cavity 362 of the cylinder 352 with the inner annular cavity 338 of the head housing 336 of the head assembly 332.

Figure 20:
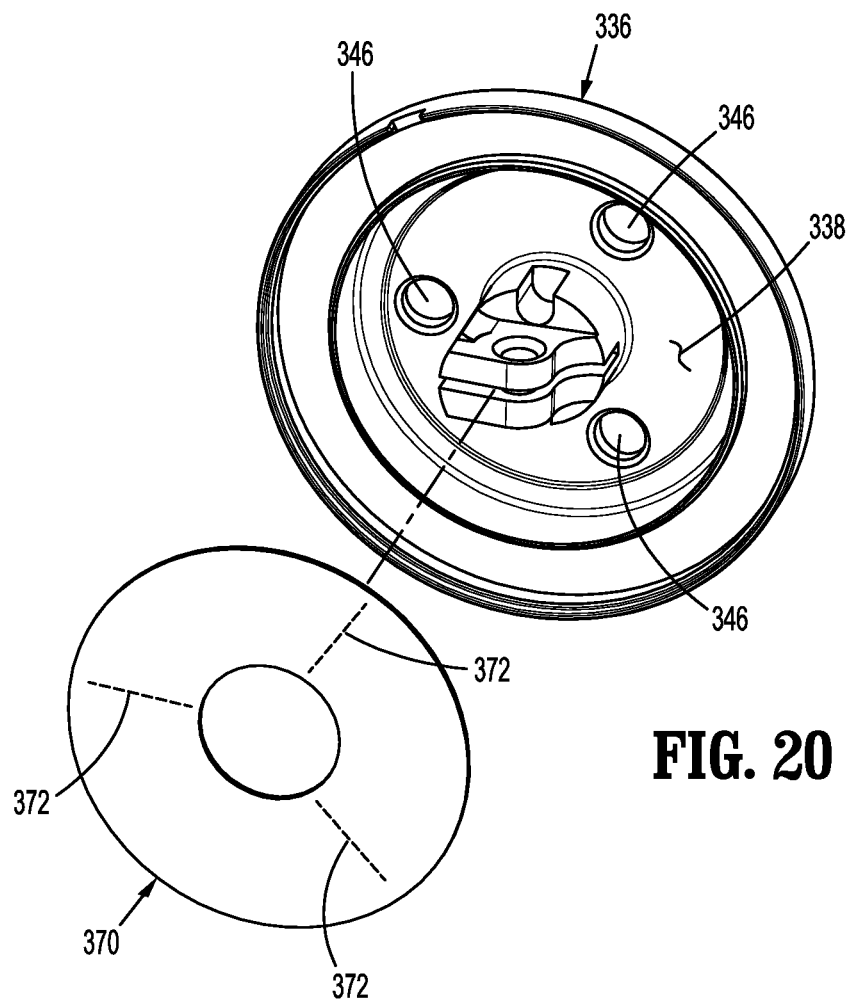
FIG. 20 is a perspective view from the proximal end of a housing of the anvil head assembly of the anvil assembly shown in FIG. 18 with a sheet of material separated from the housing.
Figure 21:
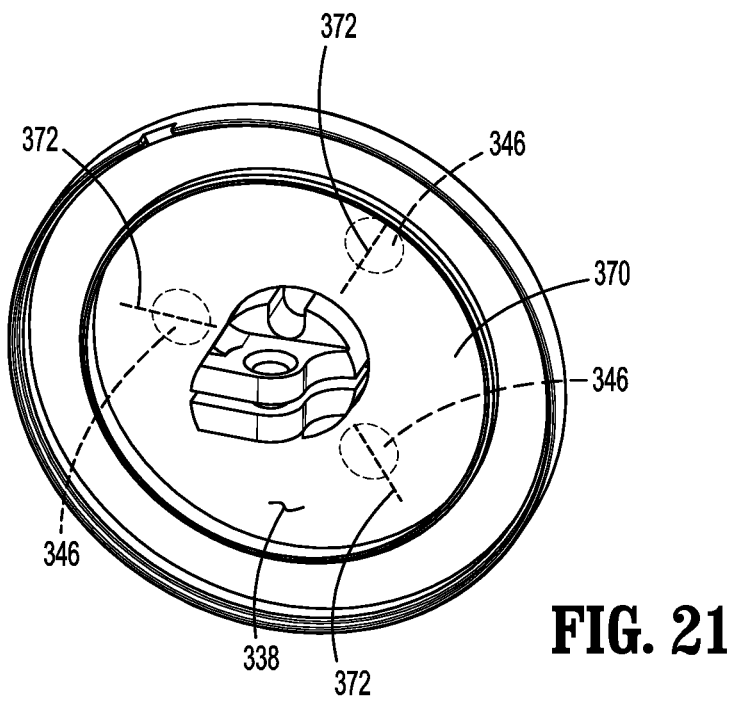
FIG. 21 is a perspective view from the proximal end of the housing of the anvil head assembly of the anvil assembly shown in FIG. 18 with the sheet of material received within the housing.

The probiotics powder 358 is retained within the distal portion of the inner annular cavity 338 by a sheet of material or membrane 370. In aspects of the disclosure, the sheet of material 370 is formed from an elastic material, such as an elastic plastic material, that includes holes or slits. In some aspects of the disclosure, the sheet of material 370 includes perforated slits 372 (FIG. 20).

Figure 22:
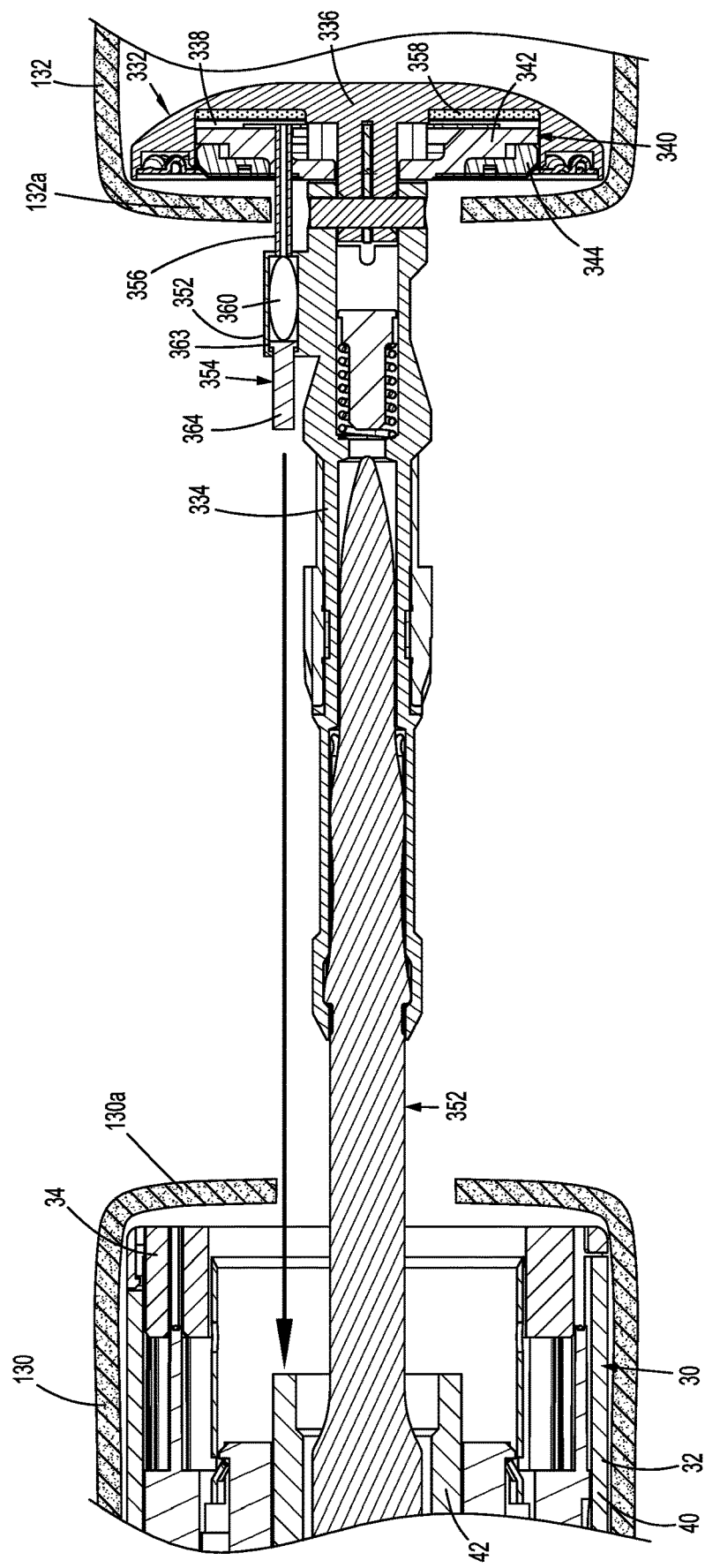
FIG. 22 is a cross-sectional view taken through a distal portion of the circular stapling device shown in FIG. 1 located with organ sections of a patient's organ with the anvil assembly shown in FIG. 18 in the open position.
Figure 23:
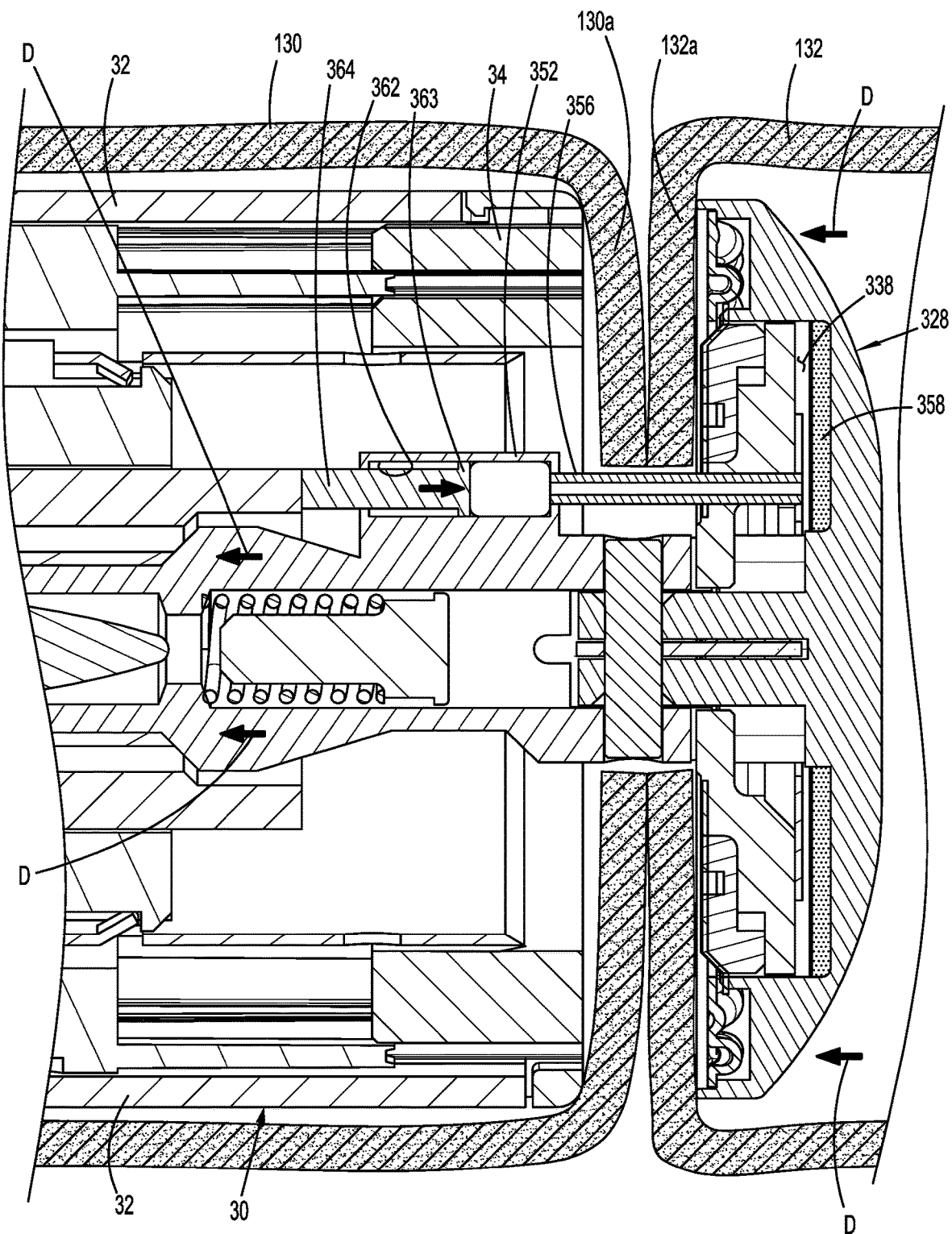
FIG. 23 is a cross-sectional view taken through the distal portion of the circular stapling device shown in FIG. 1 with the anvil assembly shown in FIG. 18 located within the organ sections of the patient's organ as the anvil assembly moves towards the clamped position.
Figure 24:
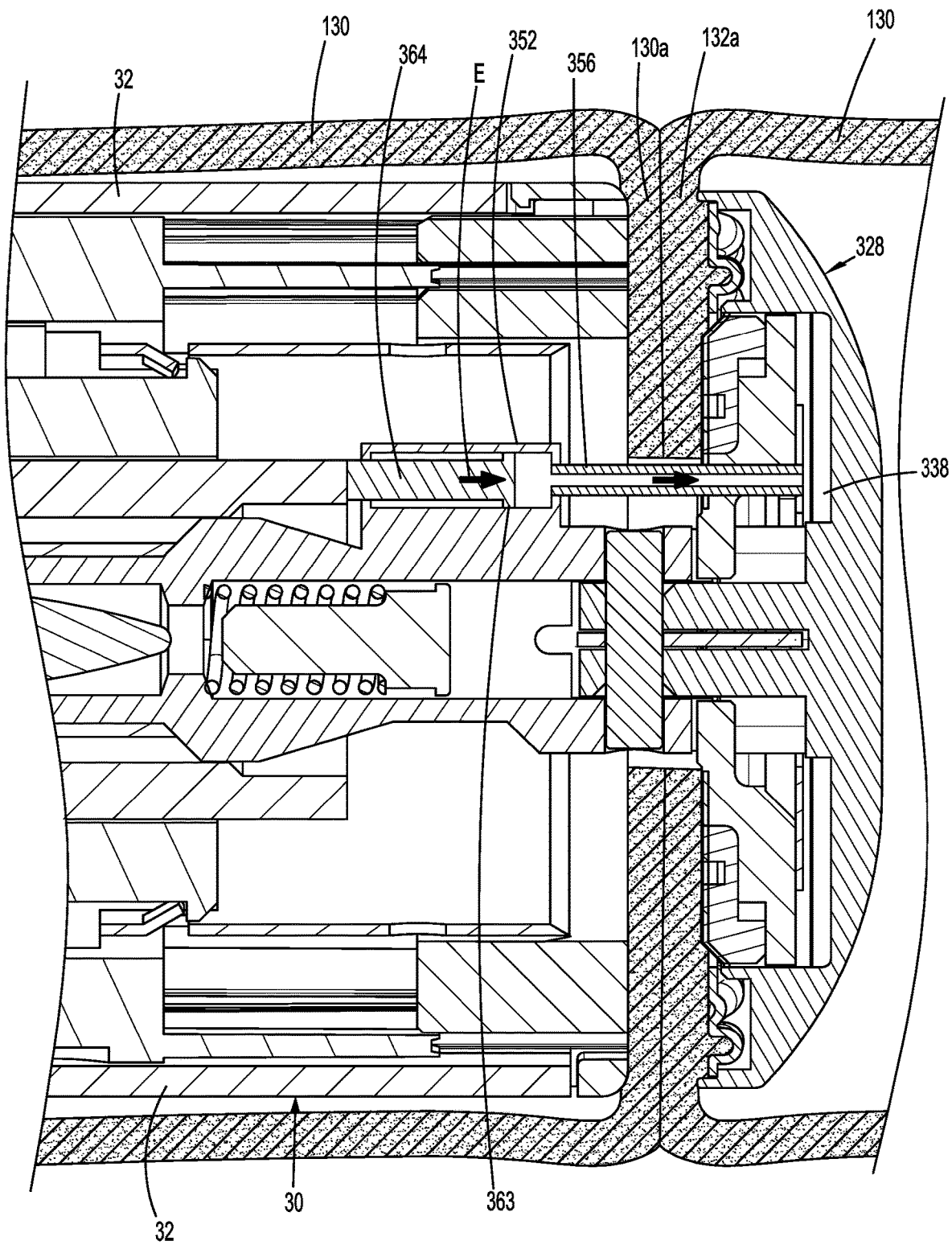
FIG. 24 is a cross-sectional view taken through the distal portion of the circular stapling device shown in FIG. 1 with the anvil assembly shown in FIG. 18 located within the organ sections of the patient's organ with the anvil assembly in the clamped position.
Figure 25:
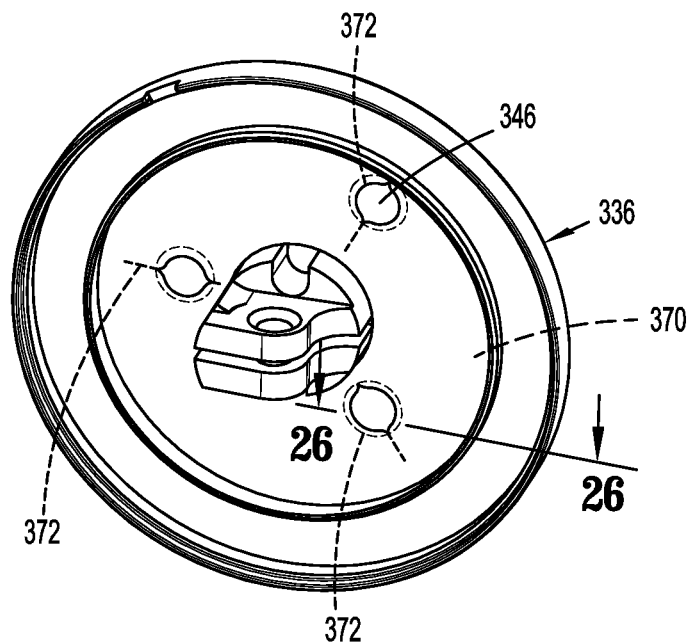
FIG. 25 is a perspective view from the proximal end of the housing of the anvil head assembly of the anvil assembly shown in FIG. 18 with the sheet of material received within the housing and perforated slits in the sheet of material open.
Figure 26:
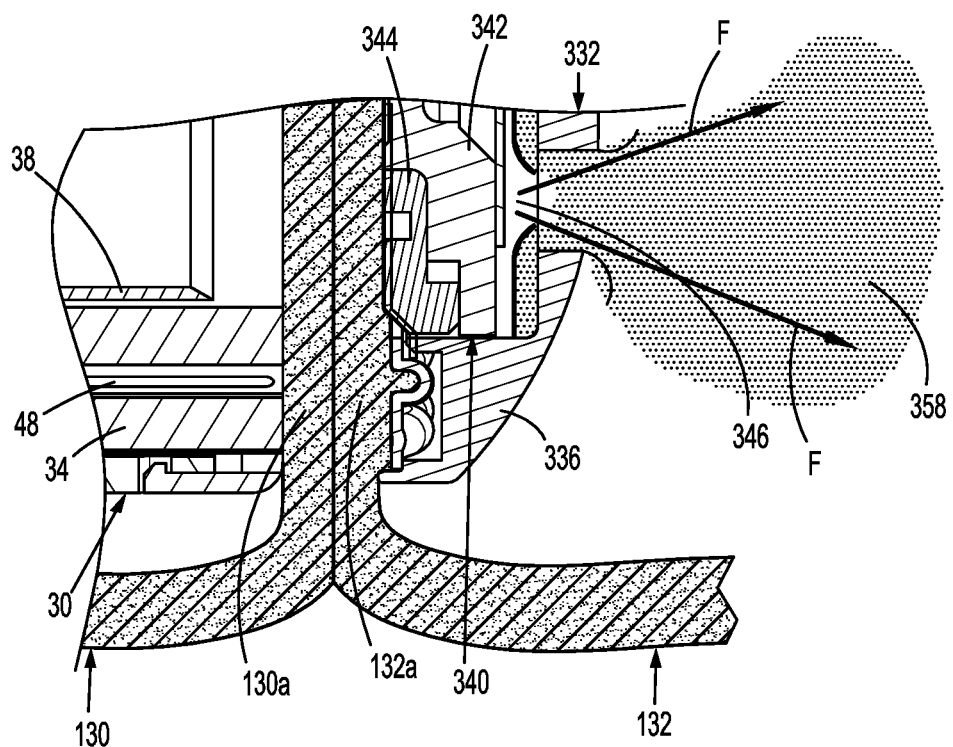
FIG. 26 is a cutaway, cross-sectional view taken through a portion of the distal portion of the circular stapling device shown in FIG. 1 with the anvil assembly in the clamped position as the probiotics exit the housing.
Figure 27:
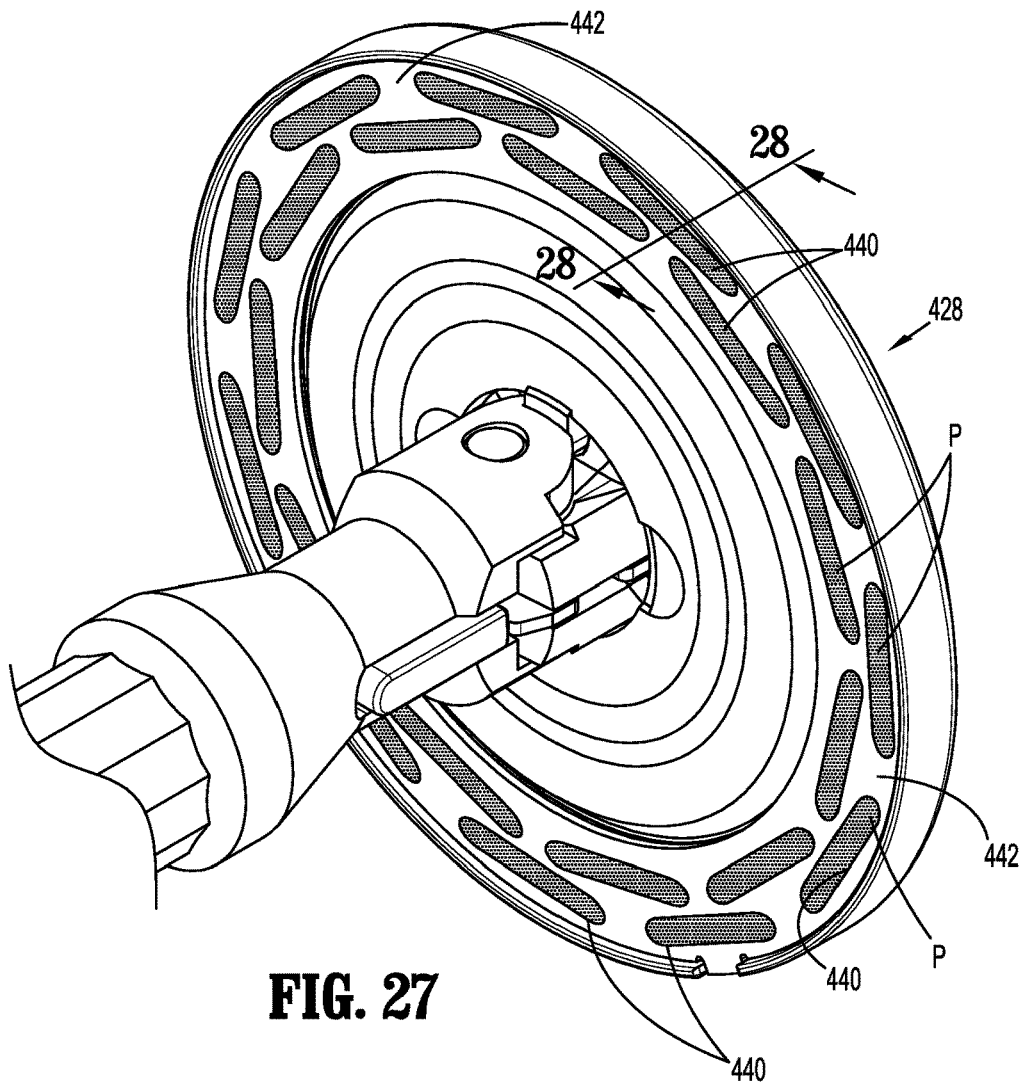
FIG. 27 is a perspective view from the proximal end of a distal portion of another alternate version of the anvil assembly of the circular stapling device shown in FIG. 1.

FIG. 22 illustrates the distal portion of the stapling device 10 (FIG. 1) with the anvil assembly 328 in an open position. In the open position, the plunger shaft 364 of the plunger 354 extends from the proximal end of the cylinder 352 and the gas filled bulb 360 is in an expanded state within the cavity 362 of the cylinder 352 with the plunger head 363 engaged with the gas filled bulb 360.

FIGS. 23-26 illustrate the distal portion of the stapling device 10 (FIG. 1) with the anvil assembly 328 in a clamped and fired position. When the anvil assembly 328 is moved from the open position to the clamped position in the direction of arrows "D" in FIG. 23 to clamp the end sections 130a and 132a of the organ sections 130 and 132 between the head assembly 332 of the anvil assembly 328 and the staple cartridge 34 of the reload assembly 30, the proximal end of the plunger shaft 364 of the plunger 354 engages a portion of the shell housing 32 to move the plunger head 363 within the cavity 362 of the cylinder 352 in the direction of arrow "E" in FIG. 23. In aspects of the disclosure, the proximal end of the plunger 354 engages the inner housing portion 42 of the shell housing 32. As the plunger head 363 moves through the cavity 362 of the cylinder 352, gas is expelled from the gas filled bulb 360 and flows through the delivery tube 356 into the inner annular cavity 338 of the head housing 336 of the head assembly 332. The increased pressure within the inner annular cavity 338 of the head housing 336 opens the slits 372 in the sheet of material 370 such that pressurized gas flows through the probiotics powder 358 to dispense the probiotics powder 358 through the openings 346 in the head housing 336 in the direction of arrows "F" in FIG. 26 onto tissue adjacent the anastomotic site.

Figure 28:
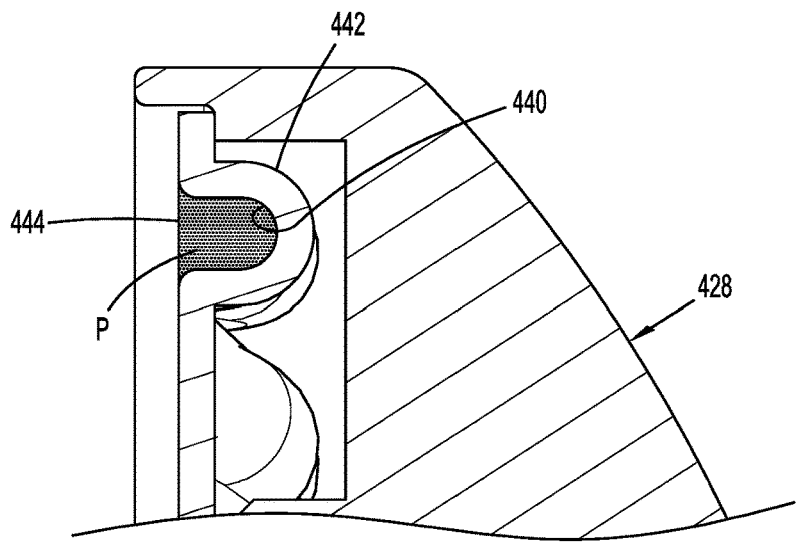
FIG. 28 is a cross-sectional view taken through section line 28-28 of FIG. 27.

FIG. 27-30 illustrate another alternate version of the anvil assembly of the stapling device 10 (FIG. 1) shown generally as anvil assembly 428. The anvil assembly 428 is substantially similar to the anvil assembly 28 (FIG. 4) but rather than have a packet 104 filled with probiotics powder 358, the probiotics "P" are positioned within staple forming pockets 440 of an anvil plate 442 of the anvil assembly 428. In aspects of the disclosure, the probiotics "P" can be in gel, powder, or liquid form. In some aspects of the disclosure, the probiotics "P" can be retained within the staple forming pockets 440 with a penetrable cover 444 (FIG. 28).

Figure 29:
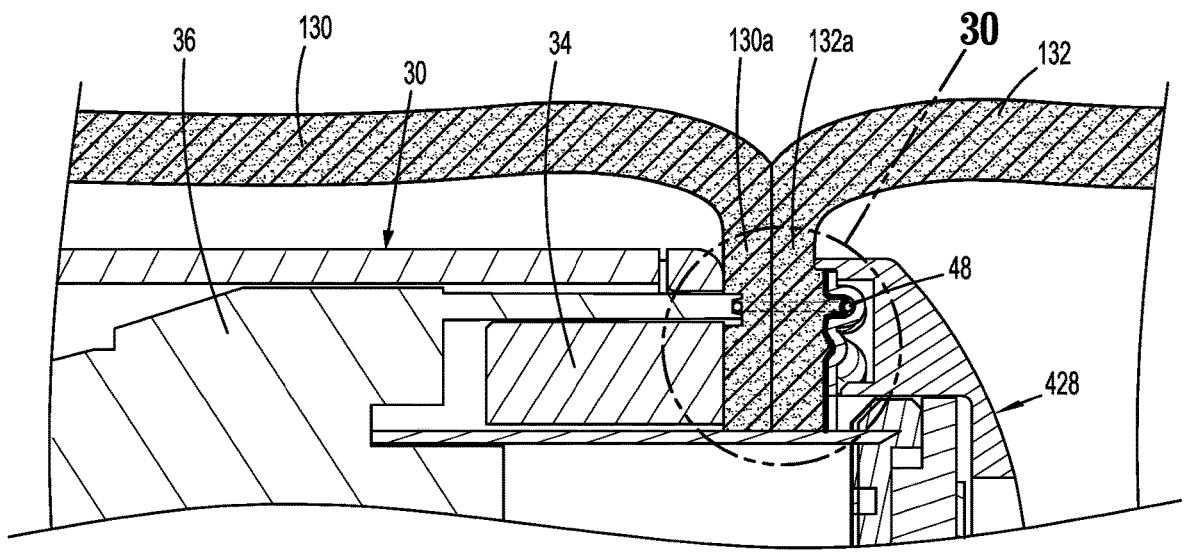
FIG. 29 is a cutaway, cross-sectional view of the circular stapling device shown in FIG. 1 with the anvil assembly shown in FIG. 27 in the clamped and fired position.
Figure 30:
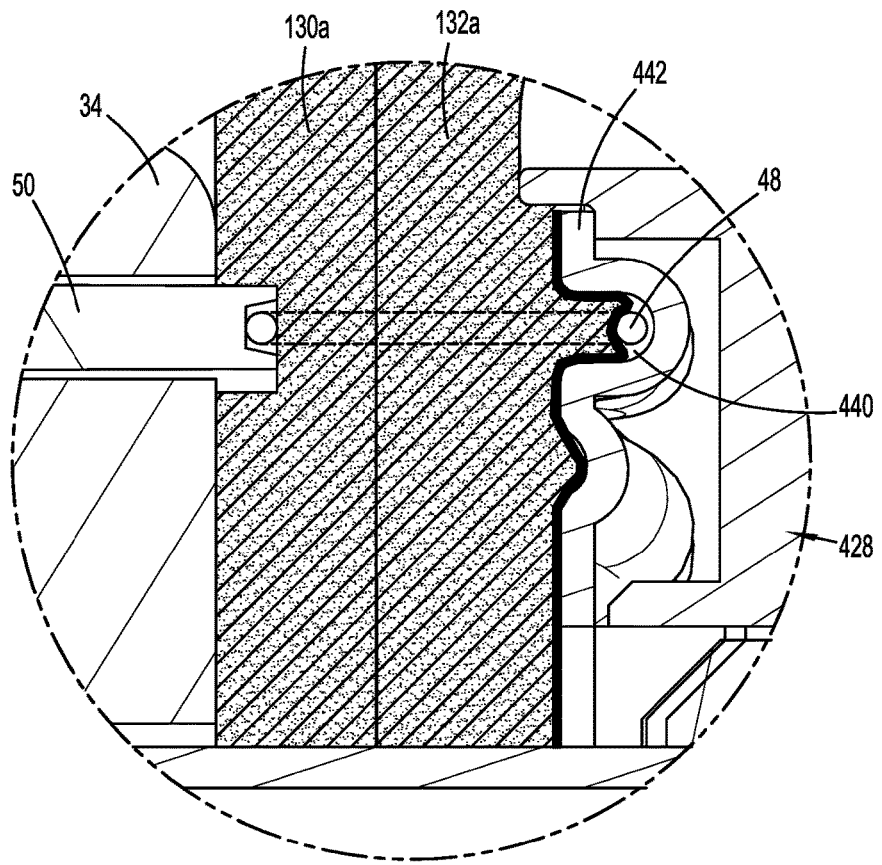
FIG. 30 is an enlarged view of the indicated area of detail shown in FIG. 29.

FIGS. 29 and 30 illustrate the anvil assembly 428 as the stapling device 10 (FIG. 1) is fired. When the stapling device 10 is fired, the staples 48 are driven from the staple cartridge 34 by fingers 50 of the pusher 36 of the reload assembly 30 into the staple forming pockets 440 of the anvil plate 442. When the staples 48 enter the staple forming pockets 440, the staples dislodge or release the probiotics "P" from the staple forming pockets 440 such that the probiotics "P" are deposited onto end sections 130a and 132a of the organ sections 130 and 132 adjacent the anastomotic site.

Figure 31:
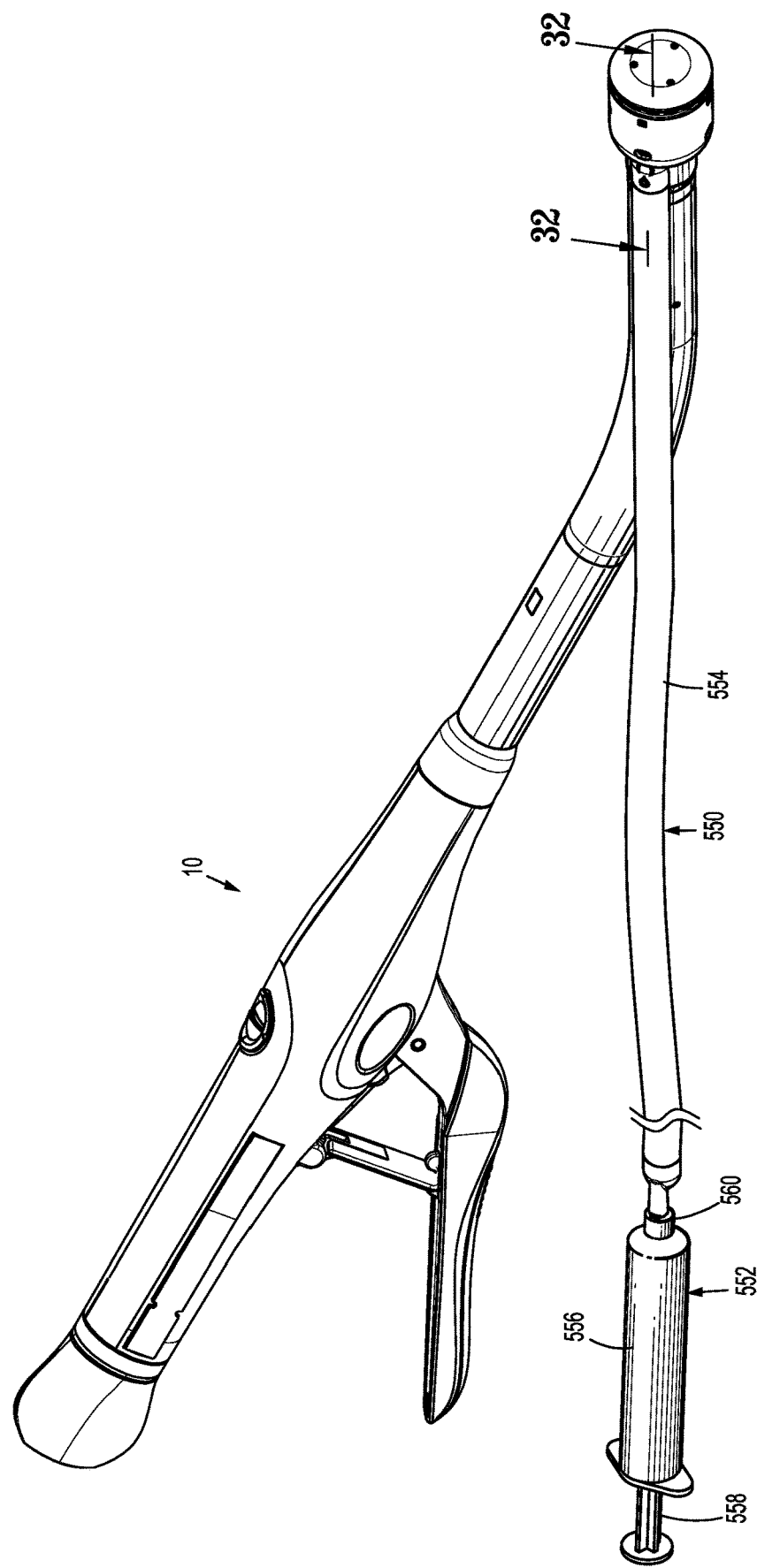
FIG. 31 is a side perspective of an alternative version of the surgical stapling device shown in FIG. 1 with a probiotics delivery system coupled to a reload assembly of the circular stapling device.
Figure 32:
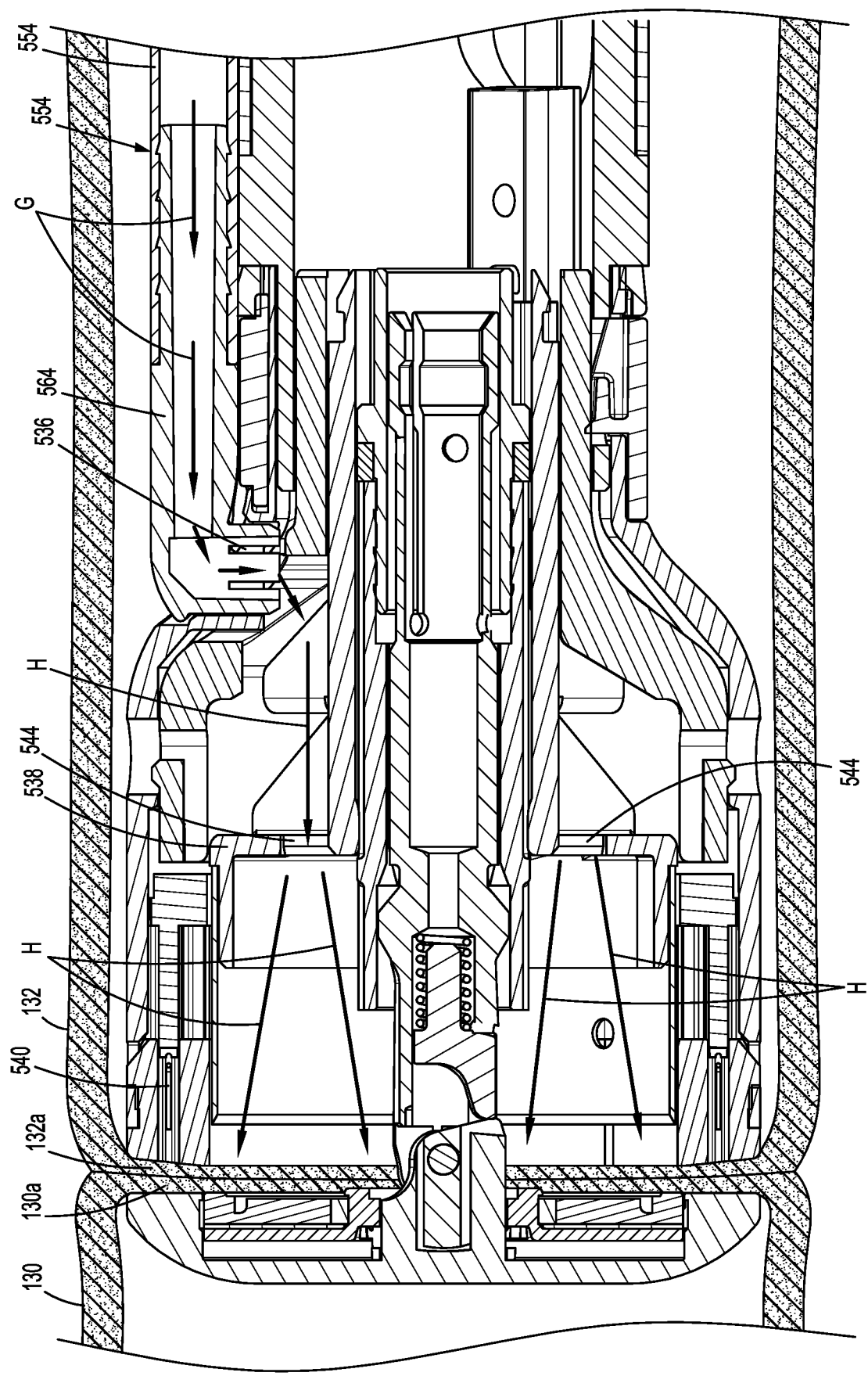
FIG. 32 is a cross-sectional view taken along section line 32-32 of FIG. 31.

FIGS. 31 and 32 illustrate the stapling device 10 (FIG. 1) shown with an alternate version of the reload assembly shown generally as reload assembly 530. The reload assembly 530 is substantially the same as the reload assembly 30 shown in FIG. 10 with a few modifications described below.

The reload assembly 530 includes a shell housing 532 that defines a cavity 534 and includes a port 536 that communicates with the cavity 534. The cavity 534 receives a pusher 538 that is movable within the cavity 534 of the shell housing 532 to eject staples 540 from a staple cartridge 542 of the reload assembly 530. The pusher 538 defines bores 544 that extend through the pusher 538 and communicate with an open distal end of the shell housing 532.

The stapling device 10 includes a probiotics delivery system 550 that includes a syringe 552 and a delivery tube 554. The syringe 552 includes a hollow body 556 that defines a cavity (not shown) and a plunger 558 that is received within the cavity of the hollow body 556. The hollow body 556 has a distal end that includes a connector 560, e.g., a luer connector, and defines an outlet port (not shown). The cavity of the hollow body 556 includes probiotics. The plunger 558 is movable in relation to the hollow body 556 to dispense the probiotics from the outlet port of the hollow body 556.

The delivery tube 554 has a proximal end that is coupled to the connector 560 of the syringe 552 and a distal end that is coupled to the port 536 of the shell housing 532. In aspects of the disclosure, the distal portion of the delivery tube 554 can be coupled to the port 536 of the shell housing by a suitable connector 564. When the plunger 558 of the syringe 552 is depressed, the probiotics within the cavity of the hollow body 556 of the syringe 552 is dispensed from the syringe 552 through the delivery tube 554 in the direction of arrows "G" in FIG. 32 and into the cavity 534 of the shell housing 532. When the probiotics enter the cavity 534 of the shell housing 532, the probiotics flow in the direction of arrows "H" in FIG. 32 through the bores 544 in the pusher 538 and is deposited onto end sections 130a and 132a of the organ sections 130 and 132 adjacent the anastomotic site.

Persons skilled in the art will understand that the instruments and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An anvil assembly comprising:
   a head assembly including a head housing, an anvil plate, and a cutting ring, the head housing defining an outer annular recess and an inner annular cavity, the anvil plate secured within the outer annular recess and the cutting ring supported within the inner annular cavity;
   a center rod assembly including a center rod having a proximal portion and a distal portion, the distal portion coupled to the head housing of the head assembly; and
   probiotics supported on the anvil assembly.

2. The anvil assembly of claim 1, wherein the head housing includes a post that is centrally located within the inner annular cavity of the head housing, the cutting ring being movable about the post within the inner annular cavity between retracted and advanced positions.

3. The anvil assembly of claim 2, wherein the head housing includes a distal inner wall that defines bores that extend through the head housing, the probiotics being supported within a packet positioned between the cutting ring and the distal inner wall of the head housing.

4. The anvil assembly of claim 3, wherein movement of the cutting ring from its retracted position towards its advanced position compresses the packet to dispense the probiotics from the packet through the bores in the head housing.

5. The anvil assembly of claim 4, further including a retainer member positioned between the inner distal wall of the head housing and the cutting ring, the retainer member including deformable tabs and being positioned to retain the cutting ring in the retracted position until a predetermined force is applied to the cutting ring.

6. The anvil assembly of claim 2, further including an container having a body, the probiotics received within the body of the container.

7. The anvil assembly of claim 6, wherein the body is positioned within the inner annular cavity of the head housing between the inner distal wall of the head housing of the anvil assembly and the cutting ring such that movement of the cutting ring from its retracted position towards its advanced position compresses the body to dispense the probiotics from the body.

8. The anvil assembly of claim 7, wherein the body is formed from plastic or glass.

9. The anvil assembly of claim 8, further including a filter positioned adjacent the body.

10. The anvil assembly of claim 9, wherein the body is formed from filter paper.

11. The anvil assembly of claim 2, wherein the probiotics are supported within the inner annular cavity of the head housing, and the center rod supports a probiotics delivery system including a cylinder, a plunger, a delivery tube, and a gas bulb positioned within the cylinder, the delivery tube communicating the cylinder with the inner annular cavity of the head housing, the plunger being movable within the cylinder to deliver gas from the gas bulb to the inner annular cavity of the head housing to dispense the probiotics through the bores in the head housing.

12. The anvil assembly of claim 11, wherein the probiotics are in powder form and are positioned between the inner distal wall of the head housing and the cutting ring.

13. The anvil assembly of claim 12, further including a sheet of material proximally of the probiotics between the cutting ring and the distal wall of the head housing, the sheet of material retaining the probiotics within the head housing.

14. The anvil assembly of claim 13, wherein the sheet of material includes perforated slits.

15. The anvil assembly of claim 1, wherein the anvil plate defines staple forming pockets and the probiotics are positioned within the staple forming pockets.

16. A surgical stapling device comprising:
an adapter assembly having a proximal portion and a distal portion, the distal portion of the adapter assembly including an anvil retainer that is movable between advanced and retracted positions;
an end effector supported adjacent the distal portion of the elongate body, the end effector including:
a reload assembly supported on the distal portion of the elongate body, the reload assembly including a shell housing, a pusher, and a staple cartridge including staples, the staple cartridge supported on the shell housing, the pusher movable within the shell housing from a retracted position to an advanced position to eject the staples from the staple cartridge; and
an anvil assembly releasably coupled to the anvil retainer and movable in relation to the staple cartridge between open and clamped positions in response to movement of the anvil retainer between its advanced and retracted positions, the anvil assembly including a head assembly and a center rod assembly, the head assembly including a head housing, an anvil plate, and a cutting ring, the head housing defining an outer annular recess and an inner annular cavity, the anvil plate secured within the outer annular recess and the cutting ring supported within the inner annular cavity, the center rod assembly including a center rod having a proximal portion and a distal portion, the distal portion coupled to the head housing of the head assembly; and
probiotics supported on the stapling device, the probiotics received within or deliverable to the end effector.

17. The stapling device of claim 16, wherein the head housing includes a post that is centrally located within the inner annular cavity of the head housing, the cutting ring being movable about the post within the inner annular cavity between retracted and advanced positions, the head housing having a distal inner wall that defines bores that extend through the head housing, the probiotics supported within a packet positioned between the cutting ring and the distal inner wall of the head housing such that movement of the cutting ring from its retracted position towards its advanced position compresses the packet to dispense the probiotics from the packet through the bores in the head housing.

18. The stapling device of claim 16, wherein the anvil assembly further includes a container having the probiotics received within the container, the container positioned within the inner annular cavity of the head housing between the inner distal wall and the cutting ring such that movement of the cutting ring from its retracted position towards its advanced position compresses the container to dispense the probiotics from the container.

19. The stapling device of claim 16, wherein the probiotics is supported within the inner annular cavity of the head housing of the anvil assembly, and the center rod of the anvil assembly supports a probiotics delivery system including a cylinder, a plunger, a delivery tube, and a gas bulb positioned within the cylinder, the delivery tube communicating the cylinder with the inner annular cavity of the head housing, the plunger being movable within the cylinder in response to movement of the anvil assembly from its open position to its clamped position to deliver gas from the gas bulb to the inner annular cavity of the head housing to dispense the probiotics through the bores in the head housing.

20. The stapling device of claim 16, wherein the anvil plate of the anvil assembly defines staple forming pockets and the probiotics are positioned within the staple forming pockets.

\* \* \* \* \*